(12) United States Patent
Zarembo et al.

(10) Patent No.: US 8,396,569 B2
(45) Date of Patent: Mar. 12, 2013

(54) LEAD ASSEMBLY AND METHODS INCLUDING A PUSH TUBE

(75) Inventors: Paul E. Zarembo, Vadnais Heights, MN (US); John S. Greenland, San Diego, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 244 days.

(21) Appl. No.: 12/785,929

(22) Filed: May 24, 2010

(65) Prior Publication Data

US 2010/0228263 A1     Sep. 9, 2010

Related U.S. Application Data

(62) Division of application No. 10/919,202, filed on Aug. 16, 2004, now Pat. No. 7,747,333.

(51) Int. Cl.
*A61N 1/00* (2006.01)
(52) U.S. Cl. ...................................................... 607/122
(58) Field of Classification Search .................. 607/122, 607/125–128; 604/175; 600/375
See application file for complete search history.

(56) References Cited

U.S. PATENT DOCUMENTS

| | | | |
|---|---|---|---|
| 1,747,407 A | 2/1930 | Wappler | |
| 4,519,404 A * | 5/1985 | Fleischhacker | 607/126 |
| 4,771,782 A | 9/1988 | Millar | |
| 4,819,661 A | 4/1989 | Heil et al. | |
| 4,850,358 A | 7/1989 | Millar | |
| 4,913,164 A * | 4/1990 | Greene et al. | 607/126 |
| 5,003,990 A | 4/1991 | Osypka | |
| 5,046,497 A | 9/1991 | Millar | |
| 5,242,431 A | 9/1993 | Kristiansen | |
| 5,304,218 A | 4/1994 | Alferness | |
| 5,381,790 A | 1/1995 | Kanesaka | |
| 5,383,924 A | 1/1995 | Brehier | |
| 5,803,928 A | 9/1998 | Tockman et al. | |
| 5,876,429 A | 3/1999 | Schroeppel | |
| 5,902,331 A | 5/1999 | Bonner et al. | |
| 6,129,749 A | 10/2000 | Bartig et al. | |
| 6,129,750 A | 10/2000 | Tockman et al. | |
| 6,185,464 B1 * | 2/2001 | Bonner et al. | 607/119 |
| 6,263,250 B1 | 7/2001 | Skinner | |
| 6,514,261 B1 | 2/2003 | Randall et al. | |
| 6,671,560 B2 | 12/2003 | Westlund et al. | |
| 6,697,677 B2 | 2/2004 | Dahl et al. | |
| 6,714,823 B1 | 3/2004 | De Lurgio et al. | |
| 6,934,589 B2 | 8/2005 | Sundquist et al. | |
| 7,747,333 B2 | 6/2010 | Zarembo et al. | |
| 7,920,927 B2 | 4/2011 | Zarembo et al. | |
| 2002/0147484 A1 | 10/2002 | Dahl et al. | |
| 2004/0068299 A1 * | 4/2004 | Laske et al. | 607/3 |
| 2008/0262588 A1 | 10/2008 | Zarembo et al. | |

\* cited by examiner

*Primary Examiner* — Eric D. Bertram
*Assistant Examiner* — Roland Dinga
(74) *Attorney, Agent, or Firm* — Faegre Baker Daniels LLP

(57) ABSTRACT

A lead assembly includes an elongate body having a conductor electrically coupled with an electrode coupled to the elongate body. The lead assembly includes a push tube extending along at least a portion of the elongate body. A distal tip is coupled to the elongate body substantially adjacent to the distal end of the elongate body. The distal tip is sized and shaped to couple with a push tube distal end. In one option, the distal tip includes a seat to receive the push tube distal end. In another option, the seat is a side rail seat and a guide wire extends along the elongate body and is slidably coupled with the side rail seat. The lead assembly includes, optionally, an active fixation device slidably coupled with a portion of the elongate body, and the active fixation device is sized and shaped to couple with the push tube.

10 Claims, 16 Drawing Sheets

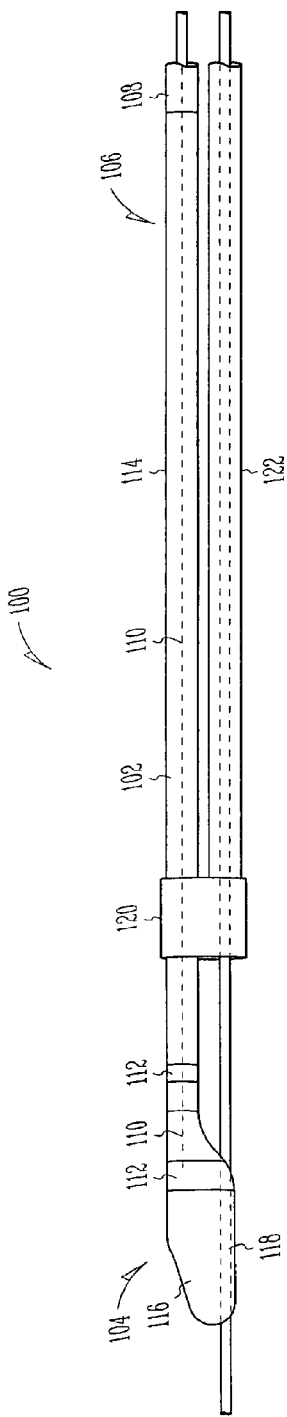
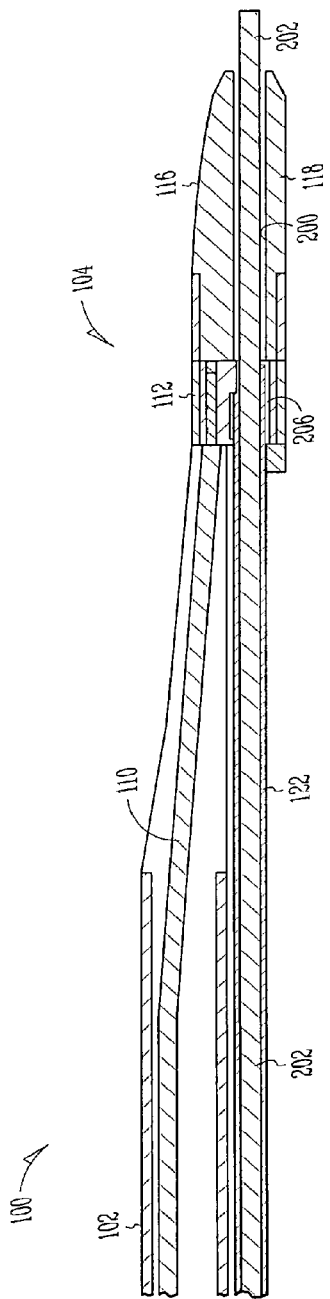
Fig. 1
Fig. 2

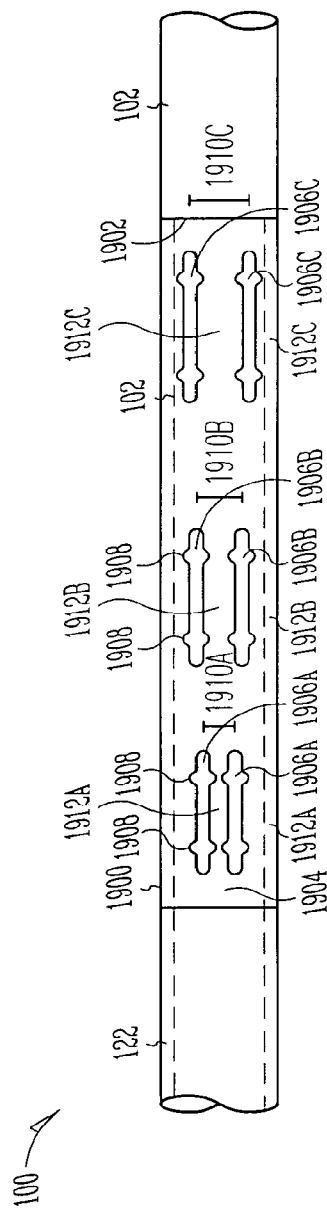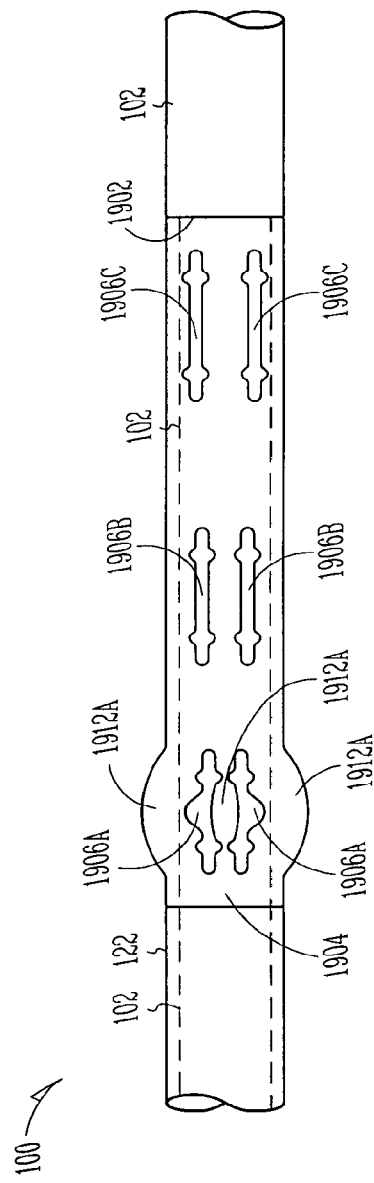

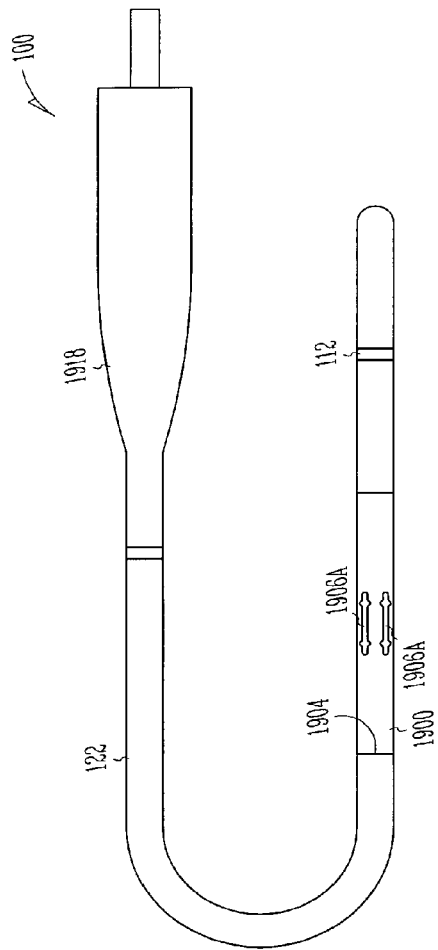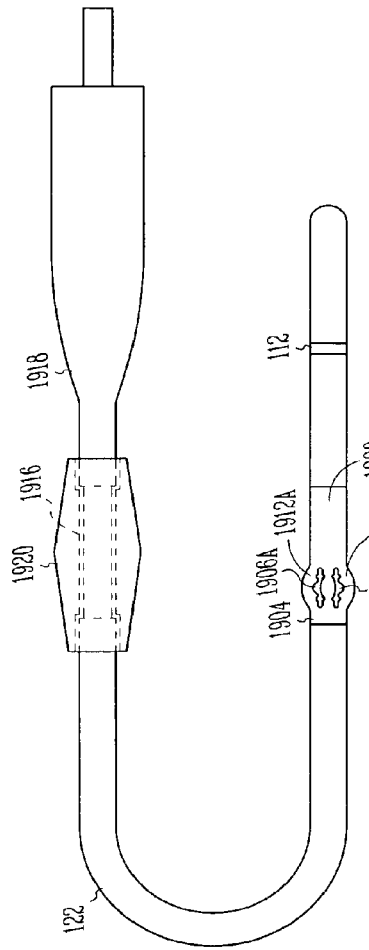
Fig. 19E
Fig. 19F

2400

2402a — GUIDE LEAD ASSEMBLY OVER GUIDE WIRE, WHEREIN GUIDE WIRE IS SLIDABLY COUPLED TO SIDE RAIL SEAT SUBSTANTIALLY ADJACENT TO DISTAL END OF LEAD ASSEMBLY, AND SIDE RAIL SET IS DISPOSED ALONG LEAD ASSEMBLY

2404 — MOVE PUSH TUBE OVER GUIDE WIRE, WHEREIN PUSH TUBE IS COUPLED TO SIDE RAIL SEAT, AND SIDE RAIL SEAT AND LEAD ASSEMBLY MOVE WITH PUSH TUBE

*Fig. 24*

LEAD ASSEMBLY AND METHODS INCLUDING A PUSH TUBE

CROSS REFERENCE TO RELATED APPLICATION

This application is a divisional of U.S. application Ser. No. 10/919,202, filed on Aug. 16, 2004, now U.S. Pat. No. 7,747,333, entitled "Lead Assembly and Methods Including a Push Tube," which is incorporated herein by reference in its entirety for all purposes. Additionally, this application is related to co-owned U.S. application Ser. No. 12/163,869, now U.S. Pat. No. 7,920,927, entitled "Lead Assembly and Methods Including a Push Tube," which is also incorporated herein by reference in its entirety for all purposes.

TECHNICAL FIELD

A lead assembly including a push tube and in particular to a lead assembly having a push tube for positioning leads and fixation devices in or around a heart.

BACKGROUND

It is often difficult to navigate flexible cardiac leads through tortuous vasculature for implantation within the vasculature or the heart. The deformable nature of some leads makes it difficult to push the lead through the twisting vasculature with a stylet. The leads bend unpredictably and lodge within the veins and arteries. Additionally, leads often include fixation features that snag on the vasculature or provide a larger profile during navigation. Leads with fixation features sometimes require multiple stylets to try navigation of the lead around corners or the like. The procedures are further complicated by enlarging the outer perimeter of leads to accommodate stylet lumens. Such lumens are often defined by coiled conductors that extend through the lead to couple with electrodes. The coiled conductors and the lumens take up space within the lead and enlarge the lead profile. Navigation of larger leads is complicated especially in tortuous vasculature, such as around the left side of the heart.

One example of an arrangement for implanting a lead is shown in U.S. Pat. No. 5,902,331. The apparatus described includes a lead having fixation features at the distal end. The lead is coupled to a guide body and moved along the guide body with a pusher wire. The fixation features of the lead are one disadvantage of this arrangement. Navigating the lead through vasculature, such as around the left side of the heart is difficult because the fixation features can undesirably lodge in vasculature tissue prior to reaching the desired implantation location. Additionally, the pusher wire is constrained from lateral movement at the distal end of the lead. If the lead becomes lodged within the vasculature the pusher wire can bow proximally to the distal end and aggravate the tissues of the vasculature. With the use of an introducing catheter around the entire arrangement the pusher wire is constrained from bowing to some extent, however the introducer catheter undesirably increases the outer perimeter of the apparatus and complicates navigation of the lead through vasculature.

Another example of an arrangement for implanting a lead is shown in U.S. Pat. No. 6,129,749. The apparatus includes a molded support body for a guide wire. The lead includes a lumen within the elongated lead body sized and shaped to receive a stylet. The stylet is used to move the lead over the guide wire into a desired orientation. One disadvantage of this arrangement is the elongated lead body is enlarged to accommodate the stylet. The lumen for the stylet is defined by a helically wound coil. The lumen and the wound coil increase the outer perimeter of the lead and navigation of the larger lead is complicated within tortuous vasculature.

U.S. Pat. No. 6,129,750 shows another example of an arrangement for implanting a lead. The apparatus includes a coil that has a naturally non-linear shape. The coil is deployed through a lumen of an over-the-wire lead and constrained from assuming the non-linear shape. When positioned where desired, the coil is released to assume the non-linear shape and engage the lead against the vessel wall. A disadvantage of this arrangement is that a coil has a relatively thick profile that is difficult to navigate through tortuous vasculature. Additionally, the coil is not securely engaged to the lead to permit rotation of the coil along with the lead to enhance contact with a desired surface within the vasculature (e.g., the myocardium of a heart).

What is needed is an assembly for positioning leads that overcomes the shortcomings of previous designs. What is further needed is an assembly capable of positioning leads and fixation devices within torturous vasculature.

SUMMARY

A lead assembly for positioning leads or placing fixation devices includes an elongate body extending from a proximal end to a distal end. In one option, at least one conductor is disposed within the elongate body and in electrical communication with at least one electrode. In another option, the electrode is coupled to the elongate body. A push tube (e.g., a tube, integral tubing to the elongate body, catheter, or the like) extends along at least a portion of the elongate body. At least a portion of the push tube is more flexible than another portion of the push tube, in one option. The push tube distal end, in one example, is more flexible than another portion of the of push tube. Optionally, at least a portion of the push tube includes a groove extending at least part way between an outer perimeter of the push tube and an inner perimeter of the push tube. A distal tip is optionally coupled to the elongate body substantially adjacent to the distal end. The distal tip, in one option, is sized and shaped to couple with a push tube distal end. In another option, the outer perimeter of the distal tip tapers from a proximal portion of the distal tip toward a distal portion of the distal tip. In yet another option, an outer perimeter of the distal tip includes a seat sized and shaped to receive a distal end of the push tube. In still another option, the elongate body is substantially adjacent (e.g. juxtaposed) to the push tube and the seat.

Optionally, at least one of the push tube distal end and the seat has a noncircular outer perimeter and the other of the push tube distal end and the seat has a corresponding inner perimeter. The seat, in yet another option, includes a socket sized and shaped to grasp and immobilize the push tube distal end. In one example, the seat includes a deformable coil disposed within the socket, and the deformable coil has an inner perimeter smaller than the outer perimeter of the push tube.

A method for positioning leads or placing fixation devices includes guiding a lead assembly over a guide wire, wherein the guide wire is slidably coupled to a side rail seat substantially adjacent to a distal end of the lead assembly. In one option, the side rail seat is disposed along the lead assembly. A push tube coupled to the side rail seat is moved over the guide wire, and the side rail seat and lead assembly move with the push tube. The push tube distal end is more flexible than another portion of the push tube, in another option. The method includes deflecting the push tube distal end (e.g. to facilitate navigation in tortuous vasculature), optionally.

Several options for the method follow. In one option, the method includes coupling the push tube with the side rail seat. Optionally, a push tube distal end is seated within a socket in the side rail seat. A surface defining the socket is sized and shaped, optionally, to immobilize at least the push tube distal end. In another option, coupling the push tube with the side rail seat includes coupling the push tube distal end having a key with the side rail seat having a corresponding recess. The method includes rotating the side rail seat and the lead assembly with the push tube, in yet another option.

In another option, an active fixation device is moved over the guide wire and/or the elongate body toward the lead assembly distal end with the push tube. The active fixation device is coupled with a distal tip coupled to the elongate body substantially adjacent to the distal end, in one option. Optionally, a combined outer perimeter of the active fixation device and the distal tip is greater than an outer perimeter of the distal tip. The active fixation device is immobilized, for instance, in surrounding tissue, by wedging the active fixation device and the distal tip within a vein or artery, in one option. In another option, the active fixation device is immobilized by expanding in surrounding tissue to engage the tissue. Immobilizing the active fixation device in surrounding tissue includes engaging a textured surface against surrounding tissue, in yet another option.

The above described assembly allows for implantation of slender leads through tortuous vasculature (e.g. coronary veins around the left side of the heart) using a push tube. In one option, the lead assembly includes a distal tip sized and shaped to couple with a push tube that extends along at least a portion of the elongate body. A pushing force is applied to the push tube and transmitted to the distal tip to push the distal end of the elongate body through vasculature and into or around the heart (e.g., into the epicardium of the heart). A portion of the elongate body proximal to the distal tip and coupled thereto is pulled as the distal tip is pushed by the push tube. In another option, the distal tip includes a seat. The push tube and the seat include, optionally, non-circular perimeters or a key and a recess. The push tube is rotated to correspondingly rotate the distal tip into a desired orientation for optimum electrode to tissue contact, in one option. In another option, the push tube is rotated to turn the distal tip and the elongate body and allow for easier navigation of the vasculature.

Because the push tube is fed over the guide wire or over the elongate body, a stylet lumen or the like is not necessary. In one option, the elongate body has a smaller cross-section and is less invasive than leads having a stylet lumen. The lead assembly includes additional conductors or the like in the space occupied by a stylet lumen, in another option. The conductors of the lead assembly described herein include cables that extend substantially linearly along the elongate body because a stylet lumen formed with coiled conductors is not necessary. Linear cables take up less space within the elongate body, as compared to coiled conductors, and allow for a lead assembly with a smaller outer perimeter that also has multiple conductors and corresponding electrodes. In yet another option, a lumen is formed within the elongate body and is sized and shaped to receive the push tube and the guide wire and the push tube is fed over the guide wire to navigate the elongate body through vasculature. Having a push tube lumen within the elongate body decreases the profile of the elongate body allowing for easier navigation of the lead assembly. Additionally, the push tube provides increased column strength compared to a stylet and facilitates transmission of increased pushing forces to the distal end of the elongate body.

Moreover, the push tube of the assembly allows for the positioning of a variety of active fixation devices into desired orientations along the elongate body, for instance, after the elongate body is positioned within vasculature and/or a heart. The elongate body tracks through the vasculature easily without the active fixation devices disposed along the elongate body until after implantation of the elongate body. In one option, the active fixation devices have a larger profile than the elongate body and are introduced after the elongate body is positioned as desired within a heart and/or the vasculature. In another option, when the active fixation device and distal tip are coupled the combined outer perimeter engages the surrounding vasculature of, for example, a vein or artery, and securely couples the elongate body with the vasculature. In another option, active fixation devices sized and shaped to deform the elongate body are advanced along the elongate body. In one option, the active fixation devices deform and push the elongate body (e.g. including electrodes) into snug engagement with the vasculature. In another option, active fixation devices are actuated with the push tube (e.g. by rotating the push tube to turn a threaded fixation device) to couple with surfaces within the vasculature or on the epicardial surfaces of a heart.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 1 is a side view illustrating a lead constructed in accordance with one embodiment.

FIG. 2 is a detailed cross-sectional view illustrating a distal portion of a lead constructed in accordance with one embodiment.

FIG. 19A is a detailed side view of a portion of a lead and an active fixation device constructed in accordance with a further embodiment.

FIG. 19B is a detailed side view of a portion of a lead and an active fixation device constructed in accordance with a further embodiment.

FIG. 19E is a side view of a lead and an active fixation device in a first unexpanded position constructed in accordance with a further embodiment.

FIG. 19F is a side view of a lead and an active fixation device in a second radially expanded position constructed in accordance with a further embodiment.

FIG. 24 is a block diagram illustrating one method of implanting a lead.

DESCRIPTION OF THE EMBODIMENTS

Figure 3:
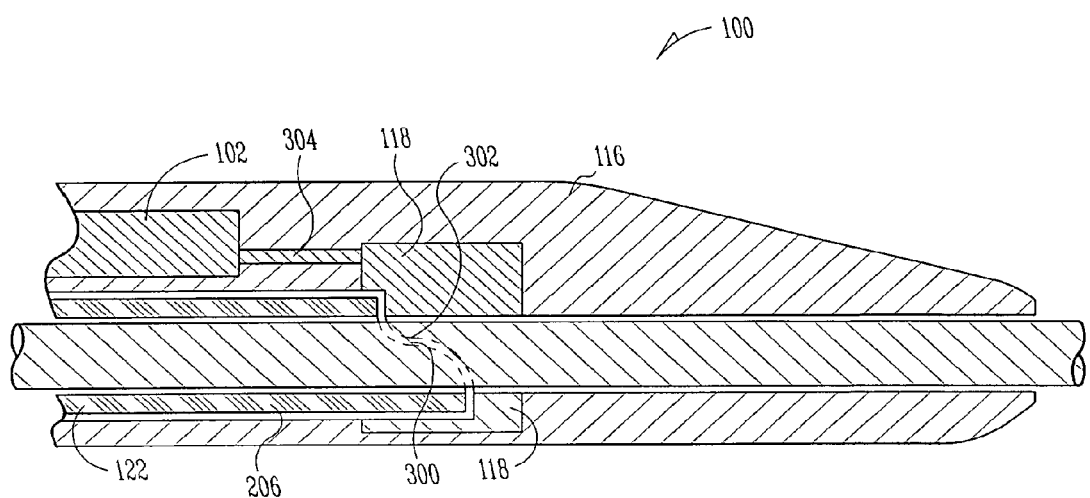
FIG. 3 is a detailed cross-sectional view illustrating a distal tip of a lead constructed in accordance with one embodiment.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

FIG. 1 is a side view of a lead assembly 100 including an elongate body 102. The elongate body 102 extends between a distal end 104 and a proximal end 106. The elongate body includes a connector terminal 108 at the proximal end 106. The connector terminal 108 is sized and shaped to couple with a pulse generator, for example, an implantable defibrillator or pacemaker. The distal end 104 includes at least one electrode 112 which electrically couples the lead assembly 100 with a heart. In another option, the electrode 112 can be a unipolar or multipolar type electrode. In still another option, multiple electrodes 112 are provided on the elongate body 102. At least one electrical conductor 110, as shown in phantom lines in FIG. 1, is disposed within the elongate body 102. The at least one electrical conductor 110 electrically couples the electrode 112 with the connector terminal 108 of the lead assembly 100. In another option, the lead assembly 100 includes multiple conductors 110 electrically coupled to multiple corresponding electrodes 112.

In one option, the elongate body 102 includes an insulating layer 114 formed of a biocompatible polymer suitable for implantation within the human body. The insulating layer 114 is made from a silicone rubber type polymer, in one option. In another option, the insulating layer 114 includes polyurethane. In yet another option, the insulating layer 114 includes polyethylene terephthalate (PTFE). In still another option, the insulating layer 114 includes ethylene-tetrafluoroethylene (ETFE), or polysiloxane urethane. The insulating layer includes other biocompatible polymers, optionally. The insulating layer 114 surrounds and insulates the conductor 110.

As shown in FIGS. 1 and 2, the lead assembly 100 includes a distal tip 116 coupled substantially adjacent to the distal end 104 of the elongate body 102. The distal tip 116 is securely coupled to the elongate body 102 to prevent relative movement, such as rotation therebetween. In one option, the distal tip 116 is adhered to the elongate body 102. The distal tip 116 is integral with the elongate body 102, in another option. Optionally, the distal tip 116, includes, but is not limited to polymers such as polyurethane, silicone rubber, polyetheretherketone, or the like. In one option, the distal tip includes polytetrafluoroethylene and/or ethylene tetrafluoroethylene for low friction. In another option, the distal tip includes a lubricious coating (e.g. a polyethylene glycol hydrophilic coating). In yet another option, the distal tip 116 is coupled to the elongate body 102 with an interference fit. In one option, the electrode 112 is coupled to the distal tip 116. The conductor 110, in another option, correspondingly extends into the distal tip 116 to couple with the electrode 112.

In one option, the lead assembly 100 includes an active fixation device 120 slidably coupled around the elongate body 102. The active fixation device 120 is sized and shaped, in another option, to engage against vasculature around a heart and immobilize at least a portion of the lead assembly 100. In yet another option, the lead assembly 100 includes a push tube 122 sized and shaped to couple with the active fixation device 120. The push tube 122 operates to translate the active fixation device 120 along the elongate body 102. In yet another option, the push tube 122 is sized and shaped to couple with the distal tip 116. Translation of the push tube 122 is transmitted to the distal tip 116 and the distal tip 116 correspondingly advances the lead assembly 100 through vasculature, such as the tortuous vasculature around the left side of a heart. The push tube 122 includes, but is not limited to, a tube, a tube integral to the elongate body, a catheter, or the like.

In another option, the distal tip 116 includes a side rail seat 118. Referring now to FIG. 2, the side rail seat 118 includes, in yet another option, a guide wire lumen 200 sized and shaped to receive a guide wire 202. The guide wire 202, optionally extends along the elongate body 102 and through vasculature to a desired location for implantation of the distal end 104 of the lead assembly 100. The guide wire 202 is slidably coupled with the inner surface of the side rail seat 118 that defines the guide wire lumen 200. In another option, at least one of the guide wire 202 and the surface defining the guide wire lumen 200 includes a lubricious coating to facilitate movement between the guide wire 202 and the side rail seat 118. The lubricious coating includes, but is not limited to, polyethylene glycol, silicone oils, fluoropolymers or the like. In one example, the lubricious coating includes SILGLIDE® a registered trademark of Applied Membrane Technology, Inc.

The lead assembly 100 includes the push tube 122, slidably coupled around the guide wire 202, optionally. The push tube 122 is a tubular member, in one option. In another option, the push tube 122 has an inner perimeter corresponding to the guide wire 202. The push tube 122 includes various cross sectional geometries, in yet another option. For example, the push tube 122 has a circular, square, ovular, triangular geometry or the like. In another example, the push tube 122 has varying cross-sectional geometries along different portions of the push tube 122. Non-circular geometries allow for transmission of rotation to the distal tip 116 optionally, as described below. The push tube 122, in one option, extends along the elongate body 102. In one example, the push tube 122 is substantially adjacent (e.g., juxtaposed) to the elongate body 102. In another option, the push tube 122 extends from at least the proximal end 106 (FIG. 1) of the elongate body 102 to the distal end 104. In one option, at least one of the guide wire 202 and the push tube 122 includes a lubricious coating to facilitate slidable movement between the guide wire 202 and the push tube 122. The push tube 122 includes a push tube distal end 206 sized and shaped to couple with the side rail seat 118.

The push tube 122, in one option, includes a material that provides sufficient column strength to transmit force along the push tube 122 to the side rail seat 118 and the distal tip 116. Optionally, the push tube 122 is constructed with a kink-resistant material to substantially eliminate kinks along the push tube 122 that prevent transmission of pushing forces along the entirety of the push tube 122. In another option, the push tube 122 is constructed with a flexible material capable of bowing and snaking through vasculature to track with the elongate body 102 during navigation of vessels. In yet another option, the push tube 122 is constructed with a material capable of transmitting rotational force along the push tube 122 to the side rail seat 118 and the distal tip 116. The push tube 122, in one example, includes, but is not limited to a super elastic material, such as Nitinol. In another example, the push tube 122 includes stainless steel. In yet another example, the push tube 122 includes a polymer, metal, composite (e.g. polymer with a metal braiding), or the like. Optionally, the push tube 122 has at least one of a coiled, slotted tube, varying wall thickness, stent-like tube and/or a tubular cable construction (i.e. a plurality of adjacent cables) to provide the push tube 122 with a desired stiffness or durometer for snaking through vasculature.

FIG. 3 is a cross sectional view showing the distal tip 116 of the lead assembly 100 and the push tube distal end 206. In one option, the push tube distal end 206 includes a recess 300. The side rail seat 118 includes a corresponding key 302 sized and shaped to engage with the push tube distal end 206. In another option, the push tube distal end 206 includes a key and the side rail seat 118 includes a recess. The recess 300 and key 302 cooperate to prevent rotation of the push tube 122 relative to the side rail seat 118 and the distal tip 116. In one option, rotation of the push tube 122 is transmitted at the push tube distal end 206 to the side rail seat 118 through cooperation of the key 302 and the recess 300. Rotation of the push tube 122, in another option, correspondingly rotates the side rail seat 118 and the distal tip 116. Optionally, rotation of the distal tip 116 twists the lead assembly 100 including the elongate body 102 into a variety of orientations and aids in navigating the lead assembly 100 through tortuous vasculature including, for instance, snags, sharp corners and the like. In one option, the distal tip 116 includes materials sufficiently rigid (e.g. stainless steel or polyetheretherketone) to transmit rotation of the push tube 122 through the side rail seat 118 to the elongate body 102. In another option, the distal tip 116 includes a deformable material such as silicone rubber, and a brace 304 extends between the side rail seat 118 and the elongate body 102 to transmit rotation of the push tube 122 to the elongate body 102 of the lead assembly 100.

Figure 4A:
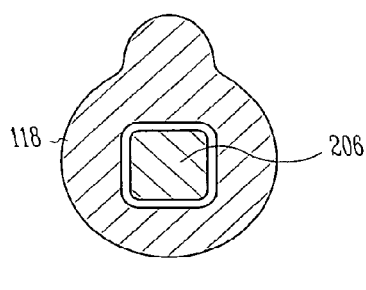
FIG. 4A is a sectional view illustrating a distal tip of a lead constructed in accordance with another embodiment.
Figure 4B:
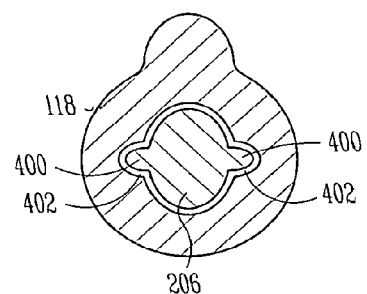
FIG. 4B is a sectional view illustrating a distal tip of a lead constructed in accordance with yet another embodiment.

FIGS. 4A and 4B show examples of non-circular geometries for the push tube distal end 206 and the side rail seat 118. The inner surface of the side rail seat 118 shown in FIG. 4A includes a square geometry. The push tube distal end 206, in one option has an outer perimeter including a corresponding square geometry. The square push tube distal end 206 and corresponding side rail seat 118 cooperate to prevent relative rotation between the push tube distal end 206 and the side rail seat 118. In another option, the push tube distal end 206 and the inner surface of the side rail seat 118 have other non-circular geometries, for instance, triangular or ovular geometries or the like. Optionally, the distal tip 116 includes a plurality of side rail seats 118 to enhance steerability of the lead assembly 100.

The push tube distal end 206 shown in FIG. 4B has a substantially circular outer perimeter. In one option, the push tube distal end 206 includes ears 400. The ears 400 are disposed within corresponding grooves 402 within the side rail seat 118. The ears 400 engage with the inner surface of the side rail seat 118 that defines the grooves 402 to prevent relative rotation between the push tube distal end 206 and the side rail seat 118. Optionally, rotation of the push tube 122 (FIG. 2) with a non-circular geometry and/or ears 400 is transmitted to the side rail seat 118 and the distal tip 116 (FIG. 1) to twist the lead assembly 100 into various orientations.

Figure 5:
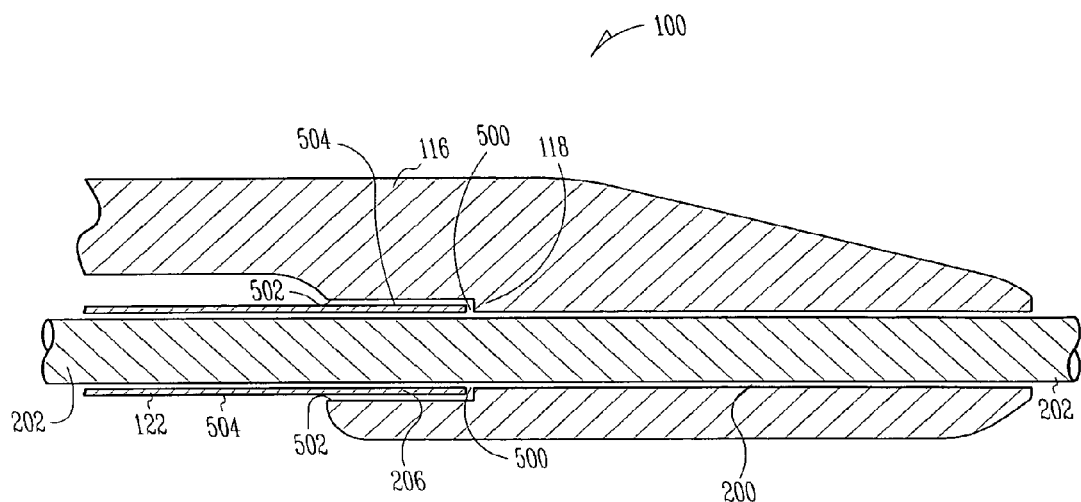
FIG. 5 is a cross-sectional view illustrating a distal portion of a lead constructed in accordance with one embodiment.

FIG. 5 is a detailed cross sectional view of the lead assembly 100 including the distal tip 116 having the side rail seat 118. The side rail seat 118 includes, in one option, a socket 500 sized and shaped to receive the push tube distal end 206 of the push tube 122. The socket 500 is optionally concentric with the guide wire lumen 200. In another option, an inner perimeter 502 of the side rail seat 118 that defines the socket 500 is sized and shaped to snugly couple with the push tube distal end 206 and immobilizes the push tube distal end 206 with respect to the distal tip 116 and the side rail seat 118. In one option, the push tube distal end 206 is securely coupled to the side rail seat 118 to substantially prevent undesired uncoupling of the push tube 122 from the side rail seat 118 during, for instance, exchange of guide wires 202. In another option, the push tube distal end 206 is securely coupled to the side rail seat 118 to substantially prevent uncoupling between the push tube 122 and the side rail seat 118 when the push tube 122 is optionally pulled toward the proximal end 106 of the elongate body 102 (FIG. 1) during navigation of the lead assembly 100.

In one option, the push tube distal end 206 includes an outer perimeter 504 slightly larger than the inner perimeter 502 of the side rail seat 118 that defines the socket 500. At least the push tube distal end 206 is optionally deformable and engages with the side rail seat 118 to form an interference fit between the push tube distal end 206 and the side rail seat 118. In another option, the outer perimeter 504 of the push tube distal end 206 includes an expandable material, such as a hydrogel or the like. The outer perimeter 504 expands from exposure to water (i.e. during implantation) and engages the inner perimeter 502 that defines the socket 500 when the push tube distal end 206 is disposed within the socket 500. In yet another option, at least one of the inner perimeter 502 of the side rail seat 118 and the outer perimeter 504 of the push tube distal end 206 includes an expandable material to securely couple the push tube 122 with the distal tip 116 and the side rail seat 118.

Figure 6:
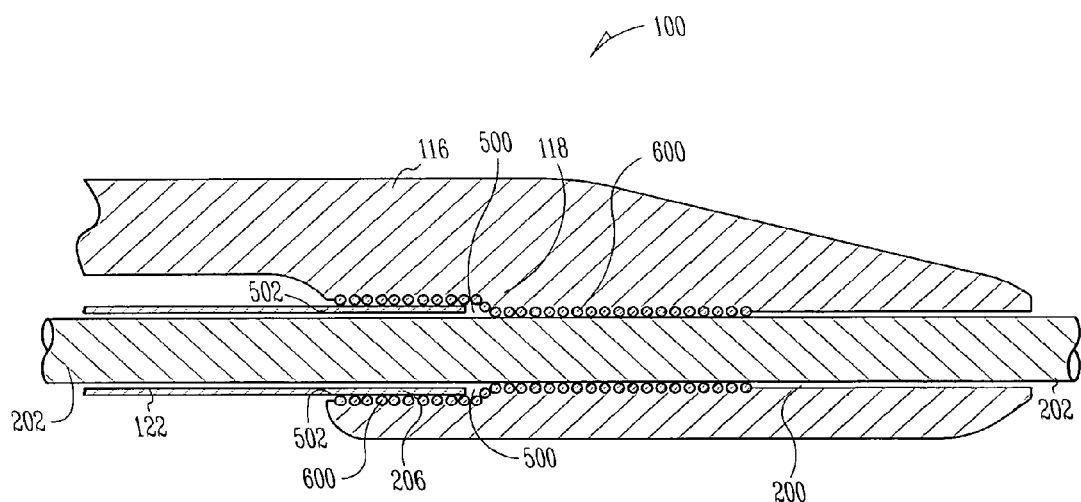
FIG. 6 is a cross-sectional view illustrating a guide wire and push tube constructed in accordance with another embodiment.

FIG. 6 is a detailed cross sectional view of the push tube 122 and the distal tip 116 including the side rail seat 118. The side rail seat 118 includes a deformable coil 600, in one option. The deformable coil 600 is disposed, at least partially in another option, within the socket 500 and defines a portion of the inner perimeter 502. In yet another option, the deformable coil 600 extends along the socket 500 and at least a portion of the deformable coil 600 surrounds the guide wire 202. Optionally, a portion of the deformable coil 600 extends into the guide wire lumen 200. The deformable coil 600 is sized and shaped to deform when the push tube 122 is received within the socket 500. In one option, the push tube 122 engages against the inner perimeter 502 of the socket 500 including the deformable coil 600 and forces the deformable coil 600 away from the guide wire 202. Deformation of the deformable coil 600 by the push tube 122 creates a restoring force within the deformable coil 600. The restoring force acts on the deformable coil 600 to tighten the deformable coil 600 around the push tube distal end 206, in another option. The deformable coil 600 is prevented from assuming the undeformed shape and snugly grasps and immobilizes the push tube distal end 206, in yet another option. As described above, the push tube distal end 206 is securely coupled to the side rail seat 118 to substantially prevent undesired uncoupling of the push tube 122 from the side rail seat 118 during, for instance, exchange of guide wires 202.

Figure 7A:
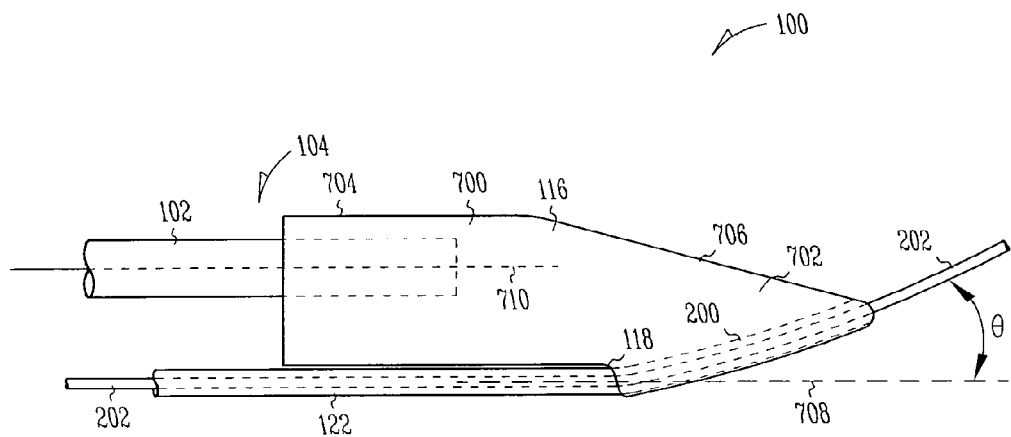
FIG. 7A is a side view illustrating a distal tip of a lead constructed in accordance with one embodiment.
Figure 7B:
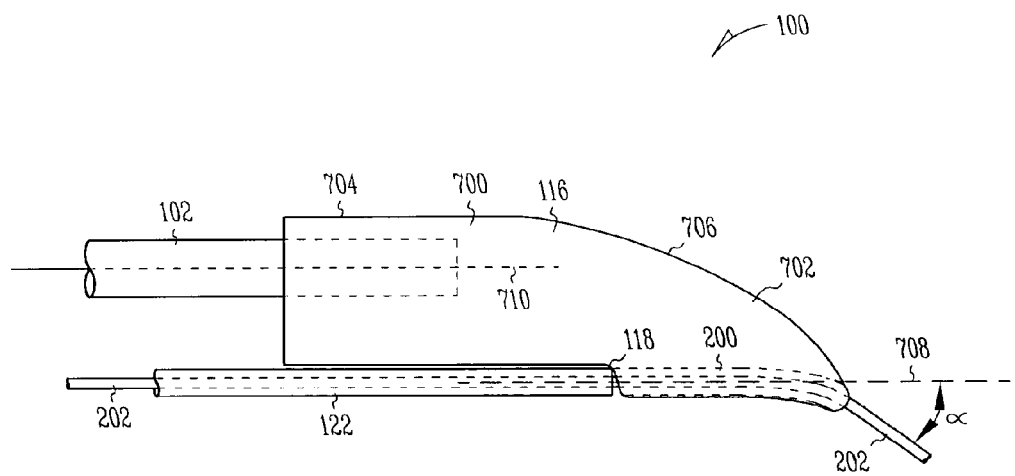
FIG. 7B is a side view illustrating a distal tip of a lead constructed in accordance with another embodiment.

FIGS. 7A and 7B are side views illustrating the guide wire 202 disposed within the side rail seat 118 of the distal tip 116. In one option, the distal tip 116 has a proximal portion 700 and a distal portion 702 and the proximal portion 700 has an outer perimeter 704 larger than an outer perimeter 706 of the distal portion 702. In another option, the distal tip 116 is tapered from the proximal portion 700 toward the distal portion 702. Tapering of the distal tip 116 gradually increases the size of the lead assembly 100 between the distal end 104 and the proximal end 106 (FIG. 1) to incorporate the guide wire 202 and the push tube 122 extending along the elongate body 102. The push tube 122, guide wire 202 and the accompanying side rail seat 118 thereby easily track with the elongate body 102 (FIG. 1) through vasculature, such as the coronary veins. The taper of the distal tip 116 reduces snagging of the distal tip 116 within vasculature and facilitates moving the lead assembly 100 around corners and bends within vessels.

In another option, shown in FIG. 7A, the guide wire lumen 200 extends through the distal tip 116 at an oblique angle θ such that the guide wire 202 extends through the side rail seat 118 at a slant relative to the distal end 104 of the elongate body 102. The guide wire 202 exits the side rail seat 118 at the oblique angle θ of the guide wire lumen 200. In yet another option, the guide wire 202 and the push tube 122 are deformable and extend from the side rail seat 118 to the proximal end 106 substantially adjacent to the elongate body 102. The oblique angle θ is optionally measured along a line 708 substantially parallel to the longitudinal axis 710 of the elongate body 102 distal end 104. The oblique angle θ, in another option is inclined relative to the longitudinal axis 710 of the elongate body 102 distal end 104. The guide wire lumen 200 with the oblique angle θ, in one option, provides an angled track for the guide wire 202 to improve tracking of the lead assembly 100 through tortuous vasculature, for instance, coronary veins. In another option, the oblique angle θ allows the lead assembly 100 to track around corners and avoid snags within the vessels.

In yet another option, shown in FIG. 7B, the guide wire lumen 200 extends through the distal tip 116 at an oblique angle α such that the guide wire 202 extends through the side rail seat 118 at a declining slant relative to the longitudinal axis 710 of the elongate body 102 distal end 104. The guide wire 202 exits the side rail seat 118 at the oblique angle α of the guide wire lumen 200. The oblique angle α is optionally measured along a line 708 substantially parallel to the longitudinal axis 710 of the elongate body 102 distal end 104. The guide wire lumen 200 with the oblique angle α, in one option, provides an angled track for the guide wire 202 to improve tracking of the lead assembly 100 through tortuous vasculature including, for example, corners, snags and the like.

In still another option, the distal tip 116 is constructed with, but not limited to, a deformable material such as silicone rubber or the like, described above. In one option, pushing the deformable distal tip 116 with the push tube 122 facilitates navigation of the lead assembly 100 around corners and snags as the distal tip 116 deforms to fit around the corners and/or through tight spaces. In another option, the distal tip includes a combination of the tapered distal tip 116, the oblique angles θ or α, and the distal tip 116 constructed with a deformable material to further enhance the tracking of the lead assembly 100 through vessels.

Figure 8:
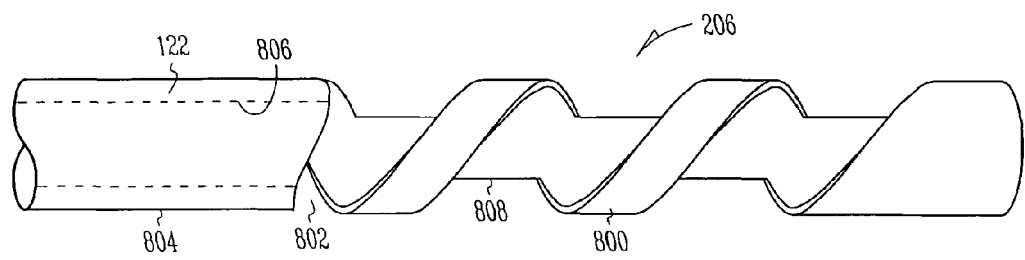
FIG. 8 is a detailed side view illustrating a push tube constructed in accordance with one embodiment.

FIG. 8 is a detailed side view of the push tube distal end 206. In one option, the push tube distal end 206 includes a flexible feature 800. The flexible feature 800 enhances the flexibility of the push tube 122 at the push tube distal end 204 to facilitate bending of the lead assembly 100 at the distal tip 116, in another option. The flexible feature 800, in one option, includes at least one groove 802 extending at least part way around the push tube 122. The groove 802 extends between the outer perimeter 804 of the push tube 122 and the inner perimeter 806 of the push tube 122, in one option. In another option, the groove 802 is scored into the outer perimeter 804 and extends between the outer perimeter 804 and an intermediate portion of the push tube 122 between the outer perimeter 804 and the inner perimeter 806. As shown in FIG. 8, in one option, the groove 802 helically extends around the push tube distal end 206 to form a spiral. The groove 802 is formed in the push tube distal end 206 by machining, laser machining, chemical etching or the like.

A strut 808 extends across the groove 802, in another option, to provide column strength to the push tube distal end 206 for axial force delivered to the side rail seat 118 and the distal tip 116 (See FIG. 1). In one option, the strut 808 is formed out of the push tube 122 during formation of the groove 802. In another option, the strut 808 is coupled to the outer perimeter 804 or inner perimeter 806 of the push tube 122. Optionally, multiple grooves 802 are formed in the push tube distal end 206 to provide the flexible feature 800. In yet another option, the flexible features 800 are formed along other portions of the push tube 122 to provide increased flexibility at various positions on the push tube 122 for enhanced navigation through vasculature.

Figure 9:
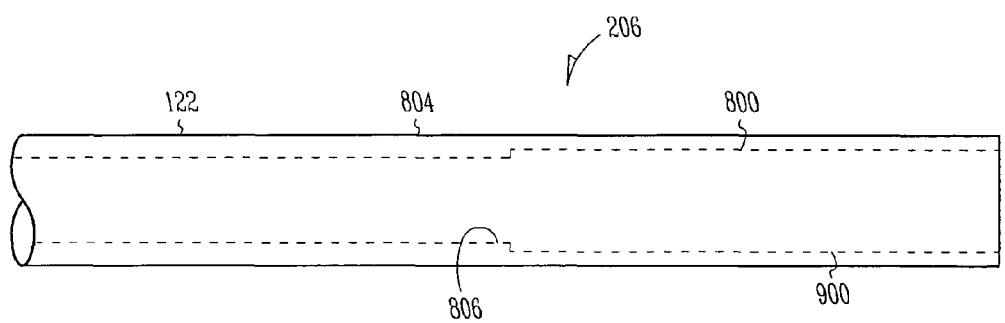
FIG. 9 is a detailed side view illustrating a push tube constructed in accordance with another embodiment.

FIG. 9 is a detailed side view of the push tube distal end 206 showing another example of the flexible feature 800. The flexible feature 800, in one option is a thin wall section 900 of the push tube distal end 206. The inner perimeter 806 of the push tube 122 is machined, etched or the like (described above), to form the thin wall section 900, in another option. In yet another option, the push tube 122 is molded to include the push tube distal end 206 with the thin wall section 900. Optionally, the thin wall section 900 is formed on the outer perimeter 804 of the push tube distal end 206. The thin wall section 900 provides additional flexibility to the push tube distal end 206 to aid in navigating the distal tip 116 of the lead assembly 100 (FIG. 1) through tortuous vasculature. With a metal push tube 122 (e.g., Nitinol), in one option, the wall thickness is between around 0.001 and 0.003 inches and the thin wall section 900 is between around 0.002 and 0.0005 inches thick. Where the push tube 122 includes polymers, optionally, the thin wall section 900 has a thickness around 0.0005 inches. The flexible feature 800, in another option includes at least one of a coiled, slotted tube, varying wall thickness, stent-like tube and/or a tubular cable construction (i.e. a plurality of adjacent cables) to provide the flexible feature 800 with a desired stiffness or durometer for snaking through vasculature.

Referring again to FIG. 2, in operation, the guide wire 202 is fed into the vasculature toward a desired location. The side rail seat 118, in one option, is coupled to the guide wire 202 with the guide wire 202 disposed in the guide wire lumen 200. The push tube 122 is slidably coupled to the guide wire 202 and moved down the guide wire 202 toward the side rail seat 118 and the distal tip 116. The distal tip 116 including the side rail seat 118, in one option, is sized and shaped to couple with the push tube distal end 206. The push tube distal end 206 couples with the distal tip 116. In one option, the push tube distal end 206 is received in a socket 500 (FIG. 5) sized and shaped to snugly couple and immobilize the push tube distal end 206, as described above. An axial pushing force is applied to the push tube 122 and transmitted along the push tube to the distal tip 116 including the side rail seat 118, in another option. The pushing force applied to the distal tip 116 operates to pull the lead assembly 100 proximal to the distal tip 116 through vessels. The push tube 122 is therefore used, in one option, to navigate the lead assembly 100 through vasculature. The push tube 122 facilitates the use of narrow flexible leads, in one option, as the push tube 122 is moved over the guide wire 202 and engaged against the side rail seat 118 to navigate the flexible leads. A stylet is unnecessary with the push tube 122. Additionally, the tubular geometry of the push tube 122 provides increased column strength to enhance transmission of the pushing force to the distal tip 116 compared to, for example, a stylet.

Referring now to FIG. 8, the push tube 122 includes a flexible feature 800, in one option. The flexible feature 800 allows the push tube distal end 206 to bend and correspondingly snake the side rail seat 118 and the distal tip 116 around corners or the like. In another option, the flexible feature 800 is positioned along the push tube 122 at various locations and improves the flexibility of the push tube 122 at the locations to improve tracking of the lead assembly 100 through tortuous vasculature.

In another option, shown in FIG. 3, at least one of the side rail seat 118 and the push tube distal end 206 include a recess 300 and a corresponding key 302. The push tube 122 is rotated, optionally, and transmits the rotation to the distal tip 116 and the side rail seat 118 by the recess 300 and the key 302. The lead assembly 100 twists with the distal tip 116. Twisting of the lead assembly improves the tracking of the lead assembly 100 around corners, snags or the like in vasculature. In yet another option, the push tube distal end 206 and the inner surface of the side rail seat 118 include corresponding non-circular geometries or ears 400 (FIGS. 4A and 4B) to transmit rotation of the push tube 122 to the distal tip 116 and the lead assembly 100.

In still another option, the guide wire 202 exits the side rail seat 118 at an oblique angle (e.g., θ or α) corresponding to an oblique angle of the guide wire lumen 200 as shown in FIGS. 7A and 7B. The lead assembly 100 follows the slanted path of the guide wire 202 through the vasculature as it is pushed over the guide wire 202 with the push tube 122, in one option. The slanted path of the guide wire 202 provides an angled track, in another option, for the lead assembly 100 to follow around corners, snags or the like.

Figure 10:
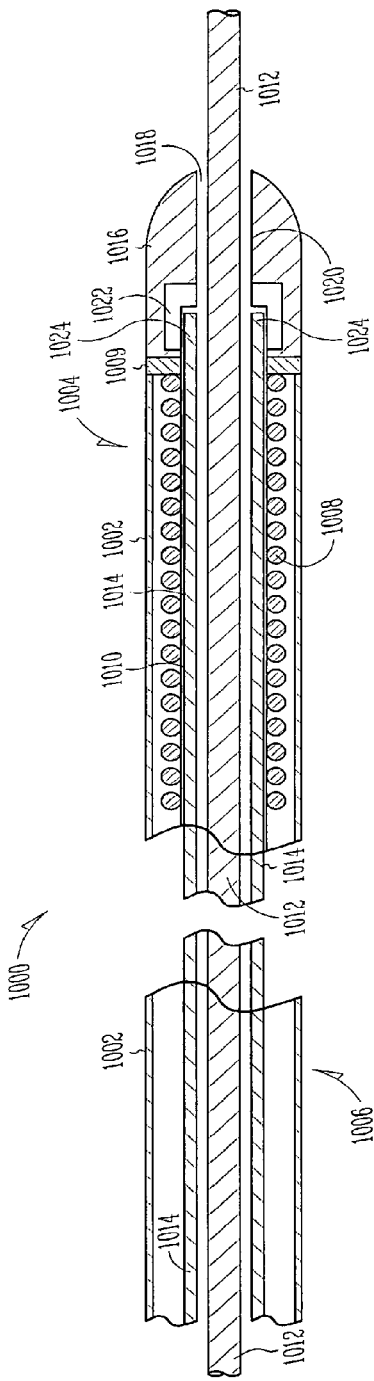
FIG. 10 is a cross-sectional view illustrating a lead constructed in accordance with another embodiment.

FIG. 10 is a cross section view of a lead assembly 1000. The lead assembly 1000 is similar in some respects to the lead assembly 100 (FIG. 1), described above. The lead assembly 1000 includes an elongate body 1002 extending from a proximal end 1006 to a distal end 1004. In the lead assembly 1000 shown in FIG. 10, at least one conductor 1008 extends from the proximal end 1006 to a location substantially adjacent to the distal end 1004. In one option, the conductor 1008 is coiled within the elongate body 1002 and forms a lead lumen 1010 sized and shaped to receive a guide wire 1012 and a push tube 1014. The lead assembly 1000 is coupled around the guide wire 1012 when the guide wire 1012 is disposed in the lead lumen 1010. In another option, the lead lumen 1010 is sized and shaped to receive the push tube 1014 without the guide wire 1012. The conductor 1008, optionally, is electrically coupled to an electrode 1009 adjacent to the distal end 1004.

The lead assembly 1000 includes, in another option, a distal tip 1016. The distal tip 1016 includes, optionally, a guide wire lumen 1018. The guide wire 1012 is sized and shaped to pass through the guide wire lumen 1018 and slidably couple with the inner surface 1020 defining the guide wire lumen 1018. The guide wire 1012 extends through the lead lumen 1010 and guide wire lumen 1018.

In another option, the distal tip 1016 includes a seat 1022 sized and shaped to receive a push tube distal end 1024. Prior to engagement with the seat 1022, the push tube 1014 is slidably coupled with the elongate body 1002. The seat 1022, in one option, grasps and immobilizes the push tube distal end 1024 as described above with the socket 500 (FIG. 5). Optionally, the push tube distal end 1024 is securely coupled to the distal tip 1016 to substantially prevent undesired uncoupling of the push tube 1014 from the distal tip during, for instance, exchange of guide wires 1012 or navigation of the lead assembly 1000. In another option, the seat 1022 provides a transition between the lead lumen 1010 and the guide wire lumen 1018. The push tube distal end 1024 engages against the seat 1022 and is prevented from entering the narrower guide wire lumen 1018, in yet another option. Pushing forces applied along the push tube 1014 are transmitted to the distal tip 1016 through engagement of the seat 1022 and the push tube distal end 1024. In one option, the push tube 1014 operates to push the distal tip 1016 and correspondingly pull the elongate body 1002 over the guide wire 1012. Optionally, the push tube 1014 is slidably coupled around the guide wire 1012 to allow the push tube 1014 and the elongate body 1002 coupled around the push tube 1014 to pass over the guide wire 1012.

In operation, a pushing force applied along a longitudinal axis of the push tube 1014 is transmitted to the seat 1022 and distal tip 1016 through engagement of the push tube distal end 1024 and the seat 1022. In one option, as the distal tip 1016 receives the pushing force through the push tube 1024, the elongate body 1002 proximal the distal tip 1016 is correspondingly pulled through the vasculature. In another option, the lead assembly 1000 passes over the guide wire 1012 and navigates vasculature as the push tube 1024 pushes the distal tip 1016 and correspondingly pulls the elongate body 1002. In yet another option, where the lead assembly does not include a guide wire 1012, the push tube 1024 transmits pushing forces to the seat 1022 and the distal tip 1016 to navigate the lead assembly 1000 through vasculature. The tubular geometry of the push tube 1024 provides increased column strength compared to, for instance, a stylet and facilitates navigation of the lead assembly in tortuous vessels.

Figure 11:
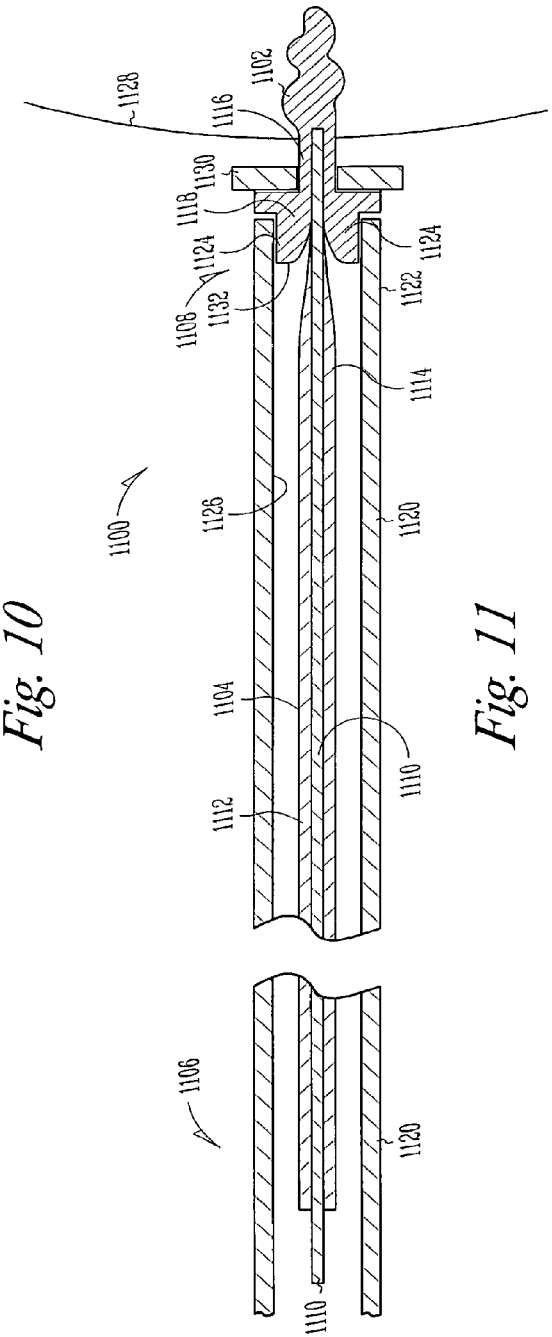
FIG. 11 is a cross-sectional view illustrating a lead constructed in accordance with yet another embodiment.

FIG. 11 is a sectional view of a lead assembly 1100 including an active fixation device 1102. The active fixation device 1102 includes threading, helically wound helix projections or the like. The lead assembly 1100 includes an elongate body 1104 extending from a proximal end 1106 to a distal end 1108. The elongate body includes a conductor 1110 extending, in one option, from the proximal end to the distal end 1108. The conductor 1110 is surrounded, in another option, by an insulating layer 1112. The insulating layer 1112, optionally, is similar to the insulating layer 114 of the lead assembly 100. In another option, the insulating layer 1112 includes a distal portion 1114 where the insulating layer 1112 narrows toward the distal end 1108 to provide increased flexibility for bending of the lead assembly 1100. Optionally, the distal portion 1114 is sufficiently flexible for the distal portion 1114 to bend at least 90 degrees around the active fixation device 1102.

A distal tip 1116 is coupled to the elongate body 1104 substantially adjacent to the distal end 1108. In one option, the conductor 1110 is electrically coupled to the distal tip 1116. The conductor 1110, in one example, is welded, soldered or bondied to the distal tip 1116. In another example, the distal tip 1116 is crimped, staked or swaged around the conductor 1110. In one option, the distal tip 1116 includes the active fixation device 1102. In another option, the active fixation device 1102 is electrically coupled to the distal tip 1116, for instance the active fixation device 1102 is integral to the distal tip 1116. In another option, the distal tip 1116 and the active fixation device 1102 are constructed with conductive metal and coupled with each other.

In one option, the distal tip 1116 includes a seat 1118 sized and shaped to receive a push tube distal end 1122 of a push tube 1120. The seat 1118 includes, in another option, an outer perimeter 1124 sized and shaped to snugly couple with the inner perimeter 1126 of the push tube distal end 1122. The push tube 1120 is slidably coupled around the elongate body 1104, in one option. In another option, the push tube distal end 1122 engages against the seat 1118 so pushing force applied to the push tube 1120 is transmitted through the push tube distal end 1122 and the seat 1118 to the distal tip 1116. Optionally, the push tube 1120 is operated to push the distal tip 1116 onto the surface 1128, for instance the epicardium of a heart. Pushing the distal tip 1116 onto the surface 1128 couples the active fixation device 1102 to the surface 1128 and securely fastens the lead assembly 1100 to the surface 1128, in another option. The push tube 1120 has sufficient column strength to engage the distal tip 1116 against the surface 1128. In one example, the push tube 1120 is constructed with a super-elastic metal, such as Nitinol. In another example, the push tube 1120 includes stainless steel. In yet another example, the push tube 1120 includes, but is not limited to, a polymer, metal, a composite (e.g., polymer tube including braided metal) or the like.

In another option, the distal tip 1116 includes a radially extending flange 1130. In one example, the flange 1130 extends substantially around the distal tip 1116. In another example, the flange 1130 extends around a portion of the distal tip 1116. In one option, the flange 1130 is electrically coupled to the conductor 1110 through the distal tip 1116 and serves as an electrode to provide electrical stimulation to the surface 1128 (e.g., the epicardium of the heart). In another option, the flange 1130 engages against a surface 1128 during insertion of the active fixation device 1102 and acts as a depth stop to prevent deeper insertion of the active fixation device 1102 into the surface 1128. The flange 1130 includes, but is not limited to, a biocompatible platinum and iridium or titanium screen mesh that promotes tissue ingrowth, in one option. In another option, the flange 1130 is constructed with, but not limited to, a polymer fiber mesh including, for instance, polyester and/or polyethylene terephthalate. Optionally, the flange 1130 includes DACRON®, a registered trademark of E.I. du Pont de Nemours and Company.

In yet another option, the seat 1118 includes a tapered mouth 1132 that substantially surrounds the elongate body 1104 as it extends into the distal tip 1116. In one option, the tapered mouth 1132 is provided around the elongate body 1104 to decrease abrasion of the insulating layer 1112 and provide a gentle slope for the elongate body 1104 to bend against after implantation of the lead assembly 1100. The tapered mouth 1132, in another option, substantially prevents the elongate body 1104 from sharply bending at the seat 1118 and thereby decreases wear on the conductor 1110 due to sharp bending.

Figure 12:
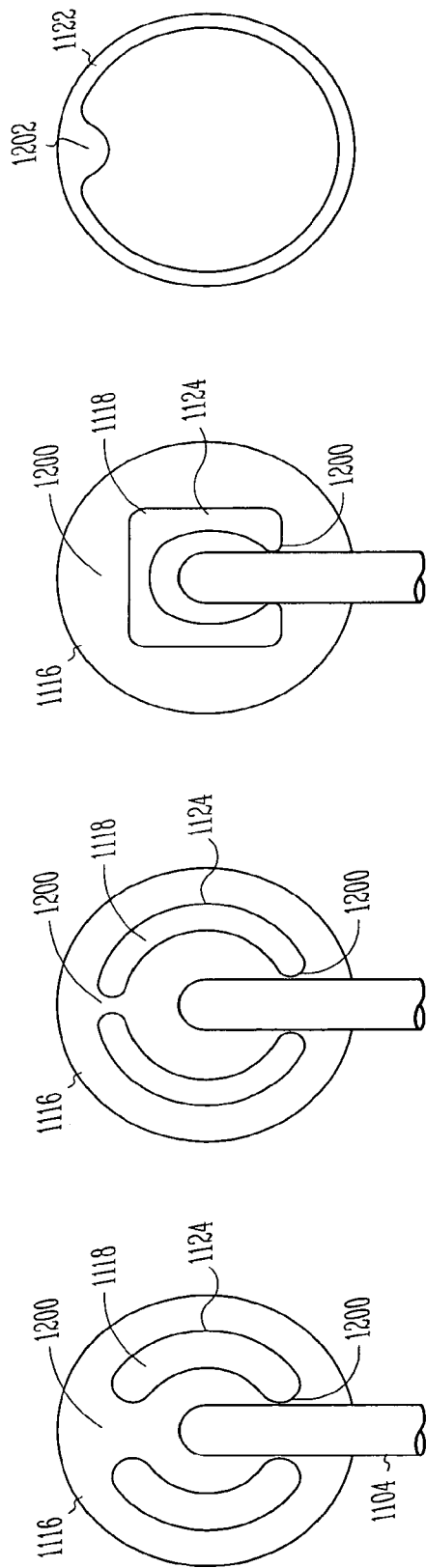
FIG. 12A is an end view illustrating a distal tip of a lead constructed in accordance with one embodiment.
FIG. 12B is an end view illustrating a distal tip of a lead constructed in accordance with another embodiment.
FIG. 12C is an end view illustrating a distal tip of a lead constructed in accordance with yet another embodiment.
FIG. 12D is an end view illustrating a push tube distal end of a push tube constructed in accordance with one embodiment.

FIGS. 12A-C are views of examples of the distal tip 1116 showing the outer perimeter 1124 of the seat 1118. FIG. 12A shows a distal tip 1116 including a seat having a substantially circular outer perimeter 1124. At least one exit groove 1200 extends from the outer perimeter 1124 toward the elongate body 1104, in one option. The exit grooves 1200, in another option, are sized and shaped to snugly receive and immobilize at least a portion of the elongate body 1104. In one option, the elongate body 1104 is bent into the exit groove 1200 after coupling the distal tip 1116 with the surface 1128 (e.g. the epicardium of the heart). The elongate body 1104 is slightly larger than the exit groove 1200 and deforms when pressed into the exit groove 1200. The portion of the seat 1118 surrounding the elongate body 1104 engages against the elongate body 1104 to grasp and immobilize the elongate body 1104.

In another option, the exit groove 1200 acts as a recess for engagement with a corresponding key 1202 on the push tube distal end 1122 (See FIG. 12D). As shown in the end view of FIG. 12D, in one option, the key 1202 is sized and shaped to fit within the exit groove 1200 of the distal tip 1116. In another option, the seat 1118 includes the key and the push tube distal end 1122 includes the recess. In yet another option, the key 1202 and the exit groove 1200 cooperate to substantially prevent relative rotation between the distal tip 1116 and the push tube 1120. Optionally, rotation of the push tube 1120 is transmitted to the distal tip 1116 and to the active fixation device 1102 (FIG. 11) by cooperation of the key 1202 with the seat 1118. The push tube 1120 operates, in one option, to drive the active fixation device 1102 (including for example, threading or a helix projection) into the surface 1128 (FIG. 11) through rotation of the distal tip 1116.

FIG. 12B is an end view of another example of distal tip 1116 including a non-circular outer perimeter 1124 for the seat 1118, such as an ovular geometry. In another example, the seat 1118 includes a square outer perimeter 1124 as shown in FIG. 12C. In yet another example, the outer perimeter 1124 of the seat 1118 is triangular, rectangular or the like. The push tube 1120 includes a corresponding non-circular push tube distal end 1122 sized and shaped to couple with the seat 1116 (See FIG. 11). Rotation of the push tube 1120 is transmitted to the distal tip 1116 and to the active fixation device 1102 by cooperation of the non-circular push tube distal end 1122 with the corresponding non-circular seat 1118. The push tube 1120 operates, in one option, to drive the active fixation device 1102 into the surface 1128 (FIG. 11) through rotation of the distal tip 1116. In another option, the seats 1118 shown in FIGS. 12B and 12C include exit grooves 1200 sized and shaped to grasp and immobilize the elongate body 1104.

In operation, the push tube 1120 is slidably coupled around the elongate body 1104 and moved toward the distal tip 1116. As shown in FIG. 11, the push tube distal end 1122 is engaged against the seat 1118 of the distal tip 1116. As described above, in one option, the non-circular inner perimeter 1126 of the push tube distal end 1122 couples around the corresponding outer perimeter 1124 of the seat 1118 to transmit rotation of the push tube 1120 to the distal tip 1116 and the active fixation device 1102 (See FIGS. 11, 12B, 12C). In another option, shown in FIG. 12D, the push tube distal end 1122 includes a key 1202 sized and shaped to fit within the exit groove 1200. The key 1202 engages with the seat 1118 to transmit rotation of the push tube 1120 to the distal end 1116 and the active fixation device 1102 (See FIGS. 12A, 12D). Rotation of the active fixation device 1102 drives the device 1102 into the surface 1128, such as the epicardium of a heart. In one option, the flange 1130 engages against the surface 1128 during rotation of the active fixation device 1102 and acts as a depth stop to prevent deeper insertion of the active fixation device 1102 into the surface 1128.

In one option, the active fixation device 1102 is electrically coupled to the conductor 1110 through the distal tip 1116. Coupling of the active fixation device 1102 with the surface 1128 electrically couples the lead assembly 1100 with the surface 1128, optionally. In another option, electrical stimulation is provided to the surface 1128 through the active fixation device 1102. In another option, the flange 1130 is electrically coupled to the conductor 1110 through the distal tip 1116 and electrical stimulation is provided to the surface 1128 through the flange 1130.

Figure 13:
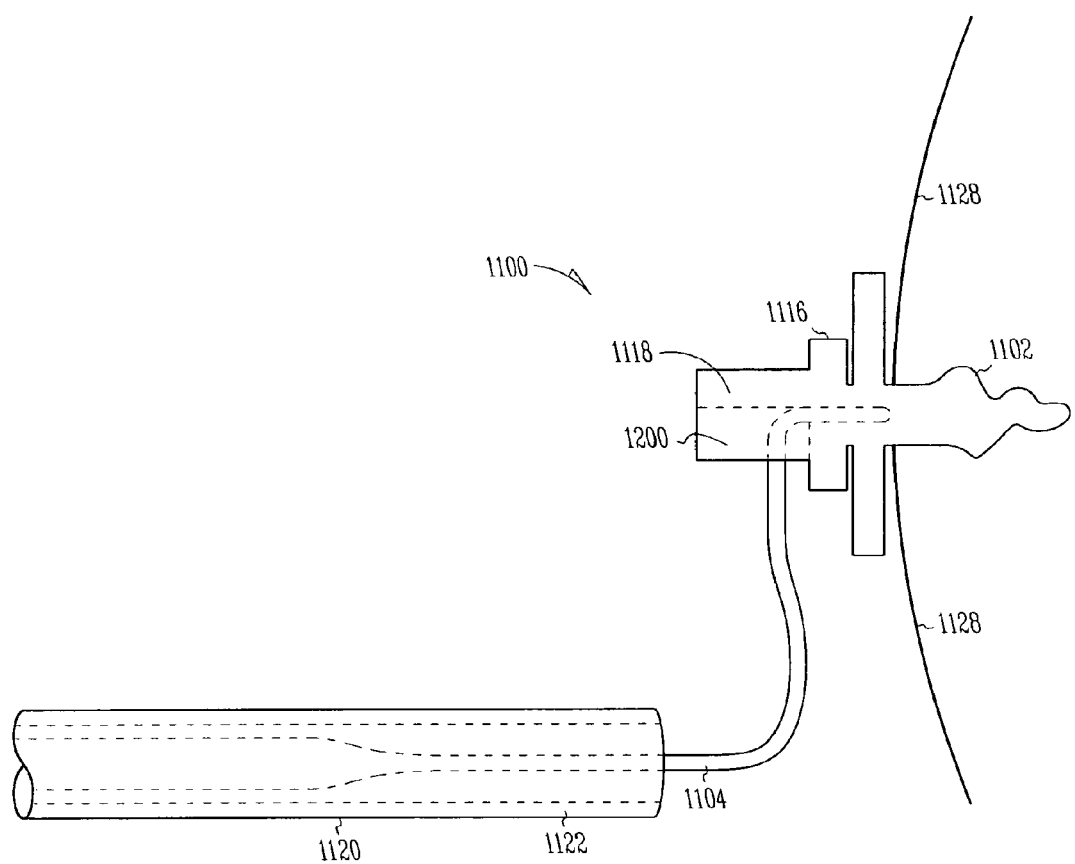
FIG. 13 is a side view illustrating a push tube and a distal tip constructed in accordance with one embodiment.

In another option, after the active fixation device 1102 couples the lead assembly 1100 with the surface 1128 the push tube 1120 is pulled away from the distal tip 1116 and the push tube distal end 1122 disengages from the seat 1118. In one option, the elongate body 1104 is lapped up against the surface 1128 to minimize wear on the lead assembly 1100 caused by, for example, chronic bending of the elongate body 1104 experienced during beating of a heart. As shown in FIG. 13, in another option, the push tube distal end 1122 sweeps the elongate body 1104 into the exit groove 1200 to immobilize the elongate body 1104 and lap the body 1104 against the surface 1128. Optionally, the push tube 1120 is uncoupled from the elongate body 1104 by pulling the push tube 1120 over the elongate body 1104 toward the proximal end 1106. In another option, the push tube 1120 is sized and shaped to split and peel away from the elongate body 1104 when withdrawn toward the proximal end 1106.

Figure 14:
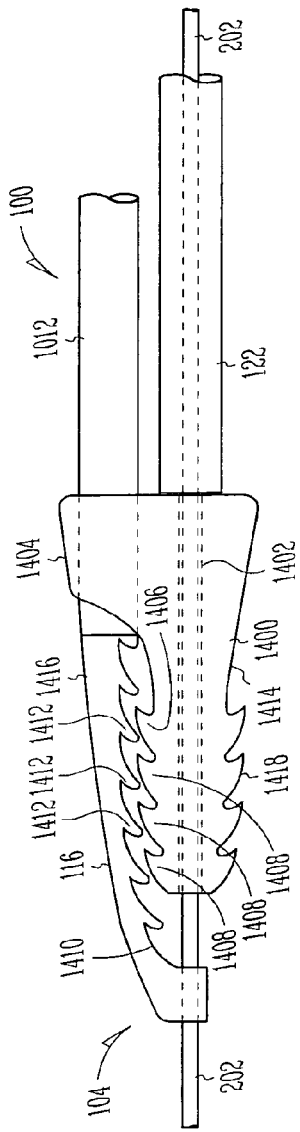
FIG. 14 is a side view illustrating a distal portion of a lead and an active fixation device constructed in accordance with one embodiment.

FIG. 14 is a side view of the lead assembly 100 including one example of an active fixation device 1400 used for, but not limited to, fixating a lead in a coronary vessel. In one option, the active fixation device 1400 includes a lumen 1402 sized and shaped to receive the guide wire 202. In another option, the active fixation device 1400 is slidably coupled around the guide wire 202. A guide projection 1404 extends from the active fixation device 1400, in yet another option. The guide projection 1404, in one option extends around the elongate body 102 and is slidably coupled to the elongate body 102. In another option, the guide projection 1404 extends at least part way around the elongate body 102. The guide projection 1404 and the lumen 1402 cooperatively ensure the active fixation device 1404 moves along the elongate body 102 and the guide wire 202, respectively. The push tube 122, optionally, engages against the active fixation device 1404 and moves the device 1404 along the guide wire 202 toward the distal tip 116. In another option, the push tube 122 is slidably coupled around the guide wire 202.

In another option, the active fixation device 1400 includes a rack 1406 of teeth 1408. The teeth 1408 are bent back along the active fixation device 1400 and point toward the proximal end 106 (FIG. 1) of the elongate body 102, in one option. An engagement surface 1410 of the distal tip 116 includes at least one pawl 1412 sized and shaped to engage against the teeth 1408 of the rack 1406. As shown in FIG. 14, in another option, the engagement surface 1410 includes multiple pawls 1412. In yet another option, the pawl 1412 points in an opposite direction from the teeth 1408. The teeth 1408 are sized and shaped to allow movement of the active fixation device 1400 over the guide wire 202 toward the distal tip 116. The teeth 1408, in one option, couple the active fixation device 1400 to the distal tip 116 by coupling with the pawl 1412. Because of the orientation of the pawl 1412 and the teeth 1408 of the rack 1406, the active fixation device 1400 is substantially prevented from moving away from the distal tip 116 when coupled to the distal tip 116, in another option. The pawl 1412 and the teeth 1408 cooperate to allow one-way movement of the active fixation device 1400 toward the distal end 104 once the device 1400 is coupled to the distal tip 116.

In yet another option, the active fixation device 1400 has a first outer perimeter 1414 and the distal tip 116 has a second outer perimeter 1416. Coupling the active fixation device 1400 with the distal tip 116 (described above) creates a combined outer perimeter that is larger than the first outer perimeter 1414 or the second outer perimeter 1416. The combined outer perimeter of the active fixation device 1400 and the distal tip 116, in one option, wedges at least the distal end 104 of the lead assembly 100 within a vessel, described below. Optionally, the outer perimeter of the active fixation device 1400 gradually increases toward the proximal end of the device 1400 to enhance engagement of the lead assembly 100 within a vessel. In another option, the active fixation device 1400 includes a textured surface 1418 sized and shaped to engage with the tissue of a vessel and couple the active fixation device 1400 and the lead assembly 100 to the vessel. The textured surface 1418, optionally, is sized and shaped to permit blood flow around the distal tip 116. The textured surface 1418 includes, for example, ridges, knurling, tines, mesh material, slots, holes or the like. In another example, the textured surface 1418 is porous and promotes tissue ingrowth to securely couple the active fixation device 1400 to the vessel. In one option, the textured surface 1418 extends substantially around the active fixation device 1400. Optionally, the active fixation device 1400 is constructed with a biocompatible material including, but not limited to, silicone rubber, polyurethane, polyetheretherketone (PEEK), ethylenetetrafluoroethylene (ETFE), titanium, or the like. In another option, the active fixation device 1400 is radio opaque.

In one option, the active fixation device 1400 is coupled to the distal tip 116 after positioning the lead assembly 100 in a desired location in the vasculature. The active fixation device 1400 is moved along the guide wire 202, in another option, with the push tube 122. In yet another option, the guide projection 1404 and guide wire 202 cooperate to ensure the active fixation device 1400 is aligned with the distal tip 116 to allow secure coupling between the distal tip 116 and the active fixation device 1400. The push tube 122 moves the active fixation device 1400 into engagement with the distal tip 116. The pawl 1412 and the teeth 1408 of the rack 1406 engage to securely couple the active fixation device 1400 to the distal tip 116. In one option, the pawl 1412 and the teeth 1408 substantially prevent movement of the active fixation device 1400 away from the distal tip 116 toward, for instance, the proximal end 106 (FIG. 1) of the elongate body 102. The push tube 122 positions the active fixation device 1400 where desired along the distal tip 116 and the pawl 1412 and the rack 1406 securely couple the device 1400 in the desired position.

In another option, once the lead assembly 100 is positioned within vasculature the active fixation device 1400 operates to securely couple the lead assembly 100 to surrounding tissue to substantially prevent dislodgement of the lead assembly 100. The combined outer perimeter of the active fixation device 1400 and the distal tip 116, in one option, is greater than the outer perimeter 1416 of the distal tip 116. In another option, when the active fixation device 1400 engages against the distal tip 116 and is coupled thereto (described above), the combined outer perimeter wedges the distal tip 116 and the active fixation device 1400 against the tissue of a vessel and lodges the lead assembly 100 within the vessel. The active fixation device 1400 includes the textured surface 1408, optionally, to increase the secure coupling of the device 1400 and lead assembly 100 to the vessel. In yet another option, the guide projection 1404 extends around the elongate body 102 and retains the active fixation device 1400 in secure engagement to the distal tip 116 after the guide wire 202 is removed from the lumen 1402.

Figure 15:
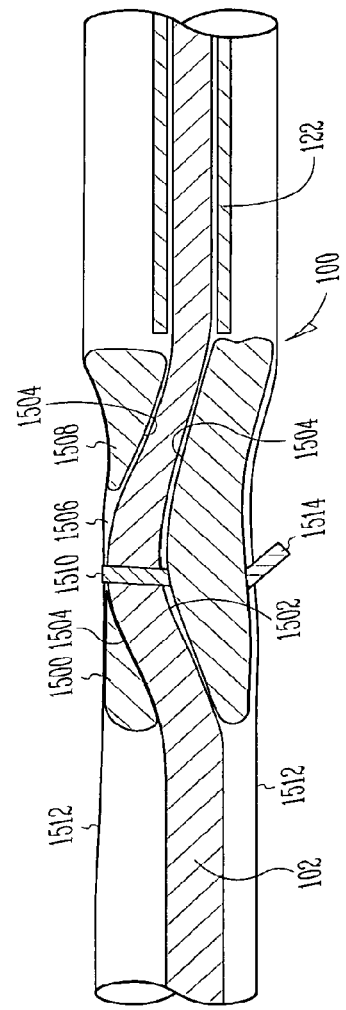
FIG. 15 is a sectional view illustrating a distal portion of a lead and an active fixation device constructed in accordance with another embodiment.
Figure 16:
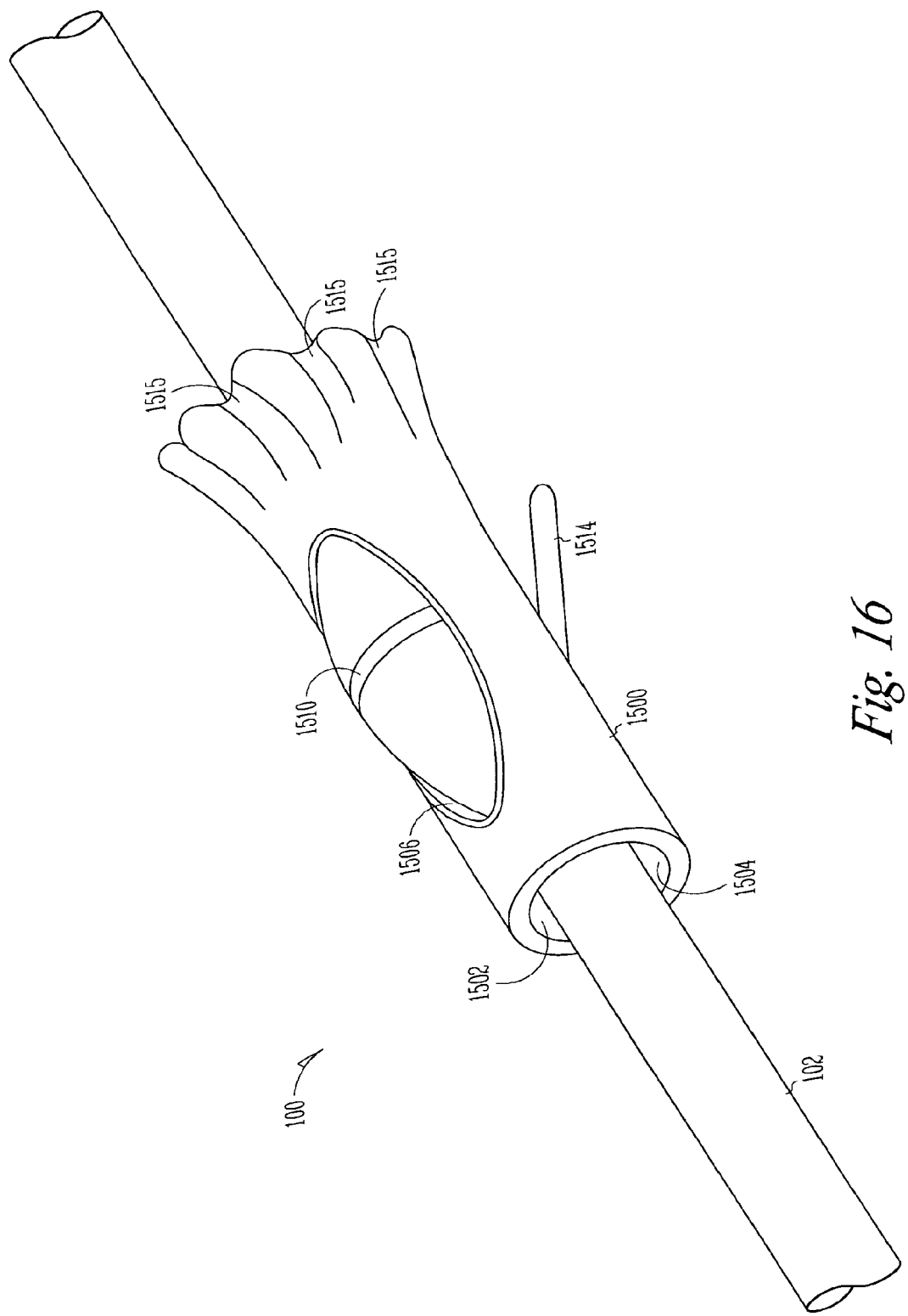
FIG. 16 is a detailed perspective view illustrating a portion of a lead and an active fixation device constructed in accordance with another embodiment.

FIGS. 15 and 16 show an active fixation device 1500 coupled around the elongate body 102. The active fixation device 1500 includes, in one option, a nonlinear arched lumen 1502. An inner surface 1504 of the active fixation device 1500 defines the non-linear arched lumen 1502 and engages against a portion of the elongate body 102. An electrode opening 1506 extends between the outer perimeter 1508 and the inner surface 1504. The portion of the elongate body 102 disposed within the arched lumen is bowed and extends through the electrode opening, in one option. In another option, the inner surface 1504 engages against the elongate body 102 and pushes the portion of the elongate body 102 through the electrode opening 1506. In one option, the elongate body 102 includes an electrode 1510 coupled around the elongate body 102 and the electrode 1510 extends, at least partially, through the electrode opening 1506. Optionally, the inner surface 1504 pushes the elongate body 102 including the electrode 1510 into contact with a surface 1512 surrounding the active fixation device 1500, such as a vein or an artery wall. In another option, the active fixation device 1500 has a sufficiently large outer perimeter 1508 so the surface 1512 engages and stretches around the device 1500. In one option, as shown in FIG. 15, the outer perimeter of the active fixation device 1500 gradually increases toward the proximal end of the device 1500 to enhance engagement of the lead assembly 100 to the surface 1512. The surrounding surface 1512, in another option, grasps the outer perimeter 1508 and immobilizes the device 1500 and the lead assembly 100. Optionally, a plurality of fixation devices 1500 are coupled around the elongate body 102. The fixation devices 1500, in one option, have differing sizes and/or textured surfaces (described below).

In another option, the active fixation device 1500 includes a textured surface, for instance at least one tine 1514. The tine 1514 engages against the surface 1512 to securely couple the active fixation device 1500 where desired along the elongate body, for example around the electrode 1510. Optionally, the tine 1514 extends from the outer perimeter 1508 toward the proximal end 106 (FIG. 1) of the elongate body 102. The tine 1514 substantially prevents movement of the active fixation device 1500 toward the proximal end 106 once the active fixation device is positioned within a vessel, such as a vein or an artery. In yet another option, the textured surface includes, but is not limited to ridges, knurling, mesh material, slots, holes or the like. In one option, shown in FIG. 16, slots 1515 extend along the active fixation device 1500 and are provided to enhance blood flow around the active fixation device 1500.

Optionally, the active fixation device 1500 includes a drug (e.g., an anti-inflammatory agent) that is emitted over time. Various drugs are placed in active fixation devices moveably coupled to the elongate body, in another option, for localized therapy where desired around a heart.

In operation, after positioning of the lead assembly 100 within the vasculature the active fixation device 1500 is guided over the elongate body 102 and pushed toward a desired position along the elongate body 102 with the push tube 122. In one option, the active fixation device 1500 is moved over the electrode 1510. The elongate body 102 including the electrode 1510 is disposed in the arched lumen 1502. The inner surface 1504 pushes the elongate body 102 and the electrode 1510 through the electrode opening 1506. In another option, when pushed through the electrode opening 1506, the electrode 1510 is engaged against a surface 1512, for instance the walls of a vein or artery. The active fixation device 1500 optionally has an oval cross section to preferentially orient the electrode 1510 within a coronary vessel and engage the electrode 1510 against the surface 1512 toward the myocardium of a heart. The curve of the elongate body 102 induced by the inner surface 1504 ensures consistent electrical communication between the surface 1512 and the electrode 1510. Additionally, deformation of the elongate body 102 by the active fixation device 1500 creates a friction fit between the elongate body 102 and the active fixation device 1500, in one option. The active fixation device 1500, in another option, increases the outer perimeter of the lead assembly 100 and thereby securely couples the lead assembly 100 to the surface 1512 at the desired position along the elongate body 102. In yet another option, the tine 1514 engages with the surface 1512 and substantially prevents movement of the active fixation device 1500 toward the proximal end 106 (FIG. 1) of the elongate body 102.

Figure 17A:
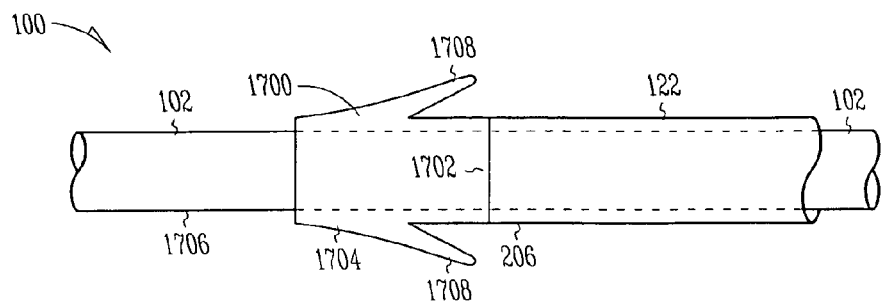
FIG. 17A is a detailed side view of a portion of a lead and an active fixation device constructed in accordance with yet another embodiment.
Figure 17B:
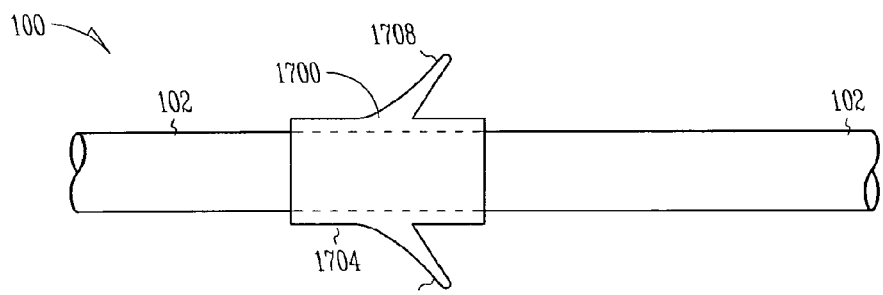
FIG. 17B is a detailed side view of a portion of a lead and an active fixation device constructed in accordance with yet another embodiment.

FIGS. 17A and 17B illustrate another example of an active fixation device 1700 slidably coupled around the elongate body 102. In one option, the push tube 122 is coupled around the elongate body 102 and the push tube distal end 206 is engaged against an end 1702 of the active fixation device 1700 (FIG. 17A). In another option, the active fixation device 1700 has an outer perimeter 1704 larger than the corresponding outer perimeter 1706 of the elongate body 102. The outer perimeter 1704, optionally, is sized and shaped to stretch surfaces of surrounding vasculature and lodge the active fixation device 1700 within the vasculature. In one option, the surrounding walls grasp and immobilize the active fixation device 1700. In another option, the active fixation device 1700 includes a deformable material (e.g. silicone rubber or the like) that deforms when surrounded and grasped by the vasculature. Deformation of the active fixation device 1700 pinches around the elongate body 102 and immobilizes the lead assembly 100 relative to the active fixation device lodged in the vasculature.

In another option, the outer perimeter 1704 of the active fixation device 1700 includes a textured surface having, for instance, ridges, knurling, mesh material or the like. In one option, the textured surface includes tines 1708. The active fixation device 1700 shown in FIGS. 17A and 17B includes two tines 1708. In another example, the active fixation device 1700 includes one or more tines 1708. The tines 1708, in another option, lay back adjacent to the outer perimeter 1704 and point toward the proximal end 106 (FIG. 1) of the elongate body 102. The tines 1708 are sized and shaped, optionally, to engage against the surfaces of the vasculature and immobilize the active fixation device 1700.

In yet another option, the outer perimeter 1704 textured surface including at least the tines 1708 is constructed with an expandable material, such as a hydrogel or the like. As shown in FIG. 17B, the tines 1708 swell as the hydrogel absorbs water from the surrounding vasculature. In one example, the expandable material includes a semi-permeable membrane that forms an outer surface of the tines 1708. The semi-permeable membrane provides an osmolarity imbalance between the tines and the fluids of the surrounding vasculature. Water permeates the membrane and swells the tines 1708 into the position shown in FIG. 17B, Prior to expansion, in one option, the tines 1708 remain substantially adjacent to the outer perimeter 1704 of the active fixation device 1700 (See FIG. 17A). In this orientation, the tines 1708 slightly alter the profile of the active fixation device 1700 and have substantially little influence on tracking of the active fixation 1700 along the elongate body 102 through the vasculature. In the expanded position (FIG. 17B) the tines 1708 curl away from the outer perimeter 1704 and substantially increase the profile of the active fixation device 1700. Expansion of the tines 1708 occurs after positioning the active fixation device 1700 optionally, where it is desirable to immobilize the lead assembly 100 within the vasculature.

In operation, the active fixation device 1700 is coupled around the elongate body 102 and moved with the push tube 122 engaged to the end 1702 of the device 1700 and also coupled around the elongate body 102. The push tube 122 pushes the active fixation device 1700 to a desired location in the vasculature, and the push tube 122 is then withdrawn. Optionally, the push tube 122 remains engaged to the active fixation device 1700 to hold the device 1700 in place along the elongate body 102. In one option, the textured surface, including the tines 1708 around the outer perimeter 1704 engage against the vasculature to immobilize the active fixation device 1700. In another option, as shown in FIG. 17B, the tines 1708, including a material such as a hydrogel or a semi-permeable membrane, expand and securely engage against the surfaces of the vasculature to immobilize the active fixation device 1700. Optionally, the active fixation device 1700 is interchangeable with other active fixation devices having different sizes and textured surfaces. In one option, a particular active fixation device is chosen based on size and the desired textured surface and coupled around the elongate body 102 and moved into a desired position with the push tube 122. Optionally, the push tube 122 is a catheter tube advanced through an outer catheter to position the active fixation device 1700 along the elongate body 102.

Figure 18A:
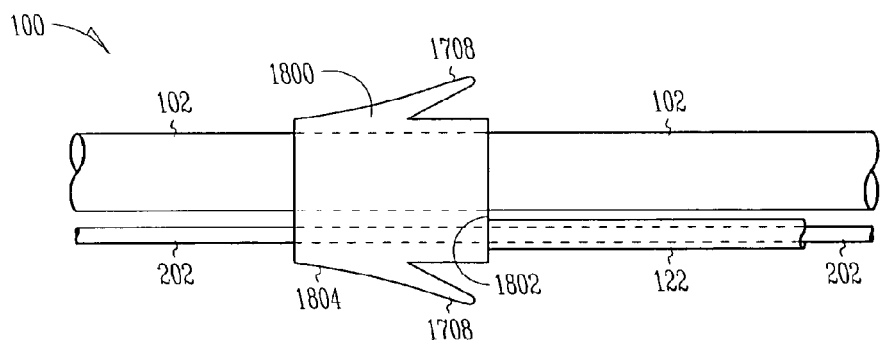
FIG. 18A is a detailed side view of a portion of a lead and an active fixation device constructed in accordance with still another embodiment.
Figure 18B:
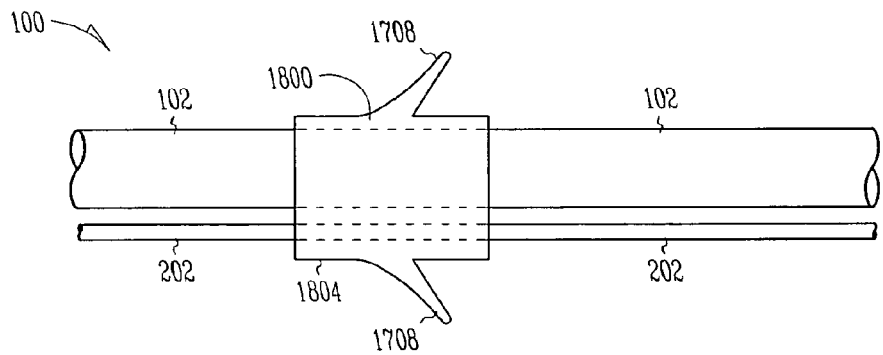
FIG. 18B is a detailed side view of a portion of a lead and an active fixation device constructed in accordance with still another embodiment.

FIGS. 18A and 18B illustrate another active fixation device 1800 similar in some respects to the active fixation device 1700 (FIGS. 17A and 17B). The active fixation device 1800 is slidably coupled around the elongate body 102. In one option, the active fixation device 1800 includes a textured surface including, for instance, tines 1708. In another example, the textured surface includes, but is not limited to, ridges, knurling, mesh material or the like. In another option, the tines 1708 include an expandable material such as a hydrogel or a semi-permeable membrane. The tines 1708, optionally, expand and curl away from the outer perimeter 1804 of the active fixation device 1800 (See FIG. 18B) to securely engage with vasculature surrounding the lead assembly 100.

The active fixation device 1800 shown in FIGS. 18A and 18B is coupled around the guide wire 202. In one option, the push tube 122 is engaged against the end 1802 of the active fixation device 1800 and coupled around the guide wire 202 (FIG. 18A). In another option, the push tube 122 is moved over the guide wire 202 and the push tube 122 correspondingly moves the active fixation device 1800 along the elongate body 102. Coupling the active fixation device 1800 around the guide wire 202 and the elongate body 102, in one option, ensures the device 1800 is retained in a desired orientation on the elongate body 102. In another option, the active fixation device 1800 is substantially prevented from rotating around the elongate body 102 during movement along the body 102 because it is coupled around the guide wire 202 adjacent to the body 102.

FIG. 19A-F are side views of an active fixation device 1900 moveably coupled around the elongate body 102. In one option, the elongate body 102 includes a flange 1902 distal to the active fixation device 1900. The active fixation device 1900 is sized and shaped to engage against the flange 1902. The push tube 122 is engaged against the proximal end 1904 of the active fixation device 1900. The push tube 122 operates to longitudinally compress the active fixation device 1900 between the flange 1902 and the push tube 122, as described below. In another option, the active fixation device 1900 is integral with the elongate body 102 distal to the active fixation device 1900. The active fixation device 1900, in yet another option, is integral to the push tube 122. The active fixation device 1900, optionally, is constructed with, but not limited to a polymer, such as polyurethane. In another option, the active fixation device 1900 is constructed with materials substantially similar to the elongate body 102.

Figure 19C:
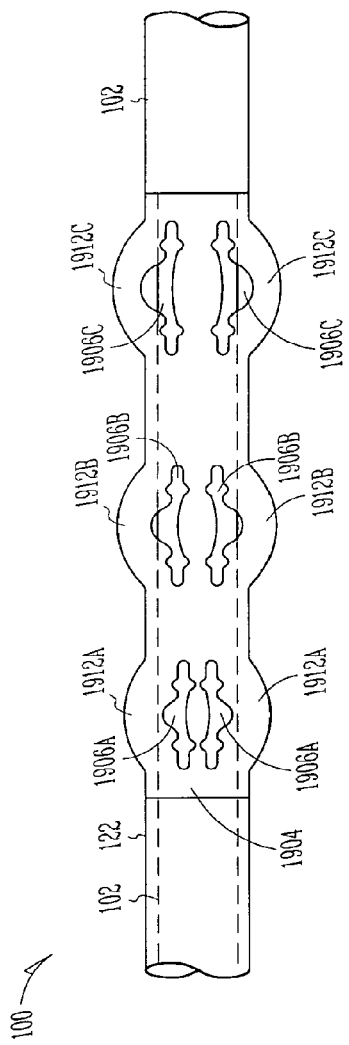
FIG. 19C is a detailed side view of a portion of a lead and an active fixation device constructed in accordance with a further embodiment.

As shown in FIG. 19A, the active fixation device 1900 includes at least one opening. In the example shown in FIGS. 19A-D, the active fixation device includes a plurality of openings 1906A-C sized and shaped to facilitate compression and radial expansion of the active fixation device 1900 when the push tube 122 is axially moved along the elongate body 102 toward the flange 1902. Members 1912A-C are disposed adjacent to the openings 1906A-C. As described below, the members 1912A-C are sized and shaped to radially expand as the active fixation device 1900 is compressed (See FIGS. 19B, C). The openings 1906A-C are formed in the active fixation device by a variety of methods, including etching, laser machining or the like. The openings 1906A-C include, in one option, recesses 1908 sized and shaped to facilitate radial expansion of the openings 1906A-C with pushing forces delivered by the push tube 122 to the active fixation device 1900. The recesses 1908, in another option, substantially prevent pinching of the members 1912A-C to close the openings 1906A-C.

In yet another option, the openings 1906A are spaced radially around the active fixation device 1900. Openings 1906B, C are also spaced radially around the active fixation device 1900, optionally. The openings 1906A are radially spaced from each other by an offset 1910A. Similarly in one option, the openings 1906B, C are radially spaced from each other by offsets 1910B, C, respectively. In one option, the offsets 1910A-C correspond to the width of the members 1912A-C. The offsets 1910A-C, gradually increase optionally from the proximal end 1904 toward the flange 1902. Increasing the offsets 1910A-C gradually increases the column strength of the members 1912A-C toward the flange 1902. The increased column strength at each set of openings 1906A-C requires progressively greater pushing forces to radially expand the members 1912A-C. As shown in FIG. 19B, increasing the offsets 1910A-C in this manner allows pushing forces transmitted by the push tube 122 to selectively expand the members 1912A adjacent the proximal end 1904 first. The members 1912B, C subsequently expand radially with the members 1912B expanding first because the offset 1910B is smaller for the members 1912B.

In one option, the openings 1906A-C increase in length between the proximal end 1904 and the flange 1902. The members 1912A-C thereby gradually increase in length between the proximal end and the flange 1902. The members 1912B, C correspondingly project further from the active fixation device 1900 than the members 1912A (FIG. 19C). The push tube 122 is advanced along the elongate body 102 to compress the active fixation device 1900 and selectively extend members 1912A-C. In one option, the active fixation device 1900 is disposed in a smaller vessel and the smaller members 1912A are only necessary to retain the elongate body 102 within the vessel, In another option, the active fixation device 1900 is disposed in a larger vessel (e.g. the vessels around a heart) and the longer members 1912B, C extend from the device 1900 with increased pushing forces applied through the push tube 122. Optionally, the members 1912A-C adjustably extend from the active fixation device 1900 in accordance with the pushing force applied through the push tube 122. In one option, greater pushing force applied through the push tube 122 causes the active fixation device 1900 to compress further and the members 1912A-C to correspondingly extend farther. The members 1912A-C adjustably extend from the active fixation device 1900 to engage against a variety of surfaces, for example vasculature with differing inner diameters.

In another option, the increasing offsets between the proximal end 1904 and the flange 1902 facilitate selective radial expansion of members 1912A-C by requiring greater and greater pushing forces to overcome the increasing column strengths provided by the progressively larger offsets 1910A-C. In one option, a physician applies a set amount of pushing force through the push tube 122 to the active fixation device 1900 to extend only the members 1912A. In another option, shown in FIG. 19C, additional pushing force is applied to extend the members 1912B and/or C.

Optionally, the offsets 1910A-C and the lengths of openings 1906A-C are varied to obtain a variety of projection profiles that extend from the lead assembly 100. For instance, offset 1910C is the smallest and the members 1912C are thereby the first to project with movement of the push tube 122 toward the active fixation device 1900. In another example, openings 1906B are the longest and thus form the largest members 1912B.

Figure 19D:
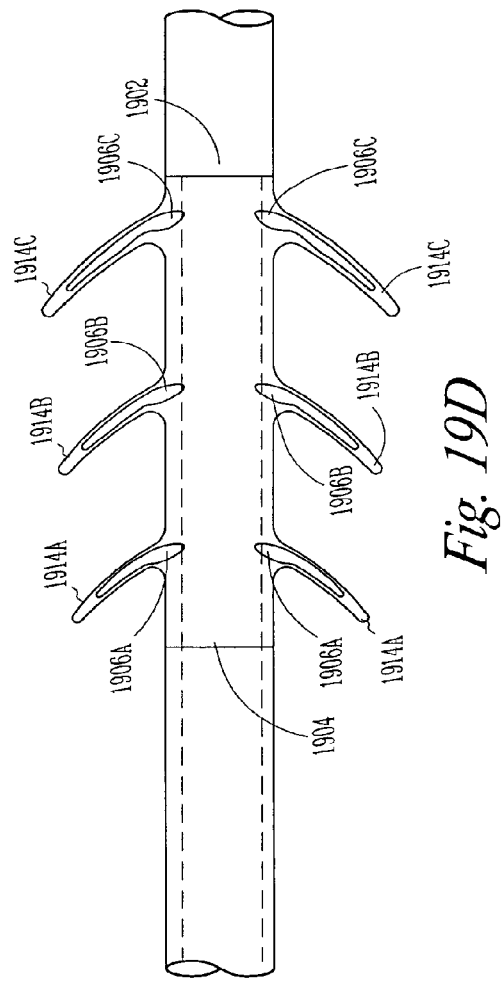
FIG. 19D is a detailed side view of a lead and an active fixation device constructed in accordance with a further embodiment.

In another option, increased pushing forces applied through the push tube 122 further longitudinally compress the active fixation device 1900, as shown in FIG. 19D. The compression of active fixation device 1900 continues to extend the members 1912A-C (FIGS. 19A-C) until the members 1912A-C fold back on themselves and form tines 1914A-C. Optionally, as with the members 1912A-C, the tines 1914B, C extend from the active fixation device 1900 further than the tines 1914A. The increased size of the tines 1914A-C relative to the radially extended members 1912A-C, in one option, provides enhanced engagement of the active fixation device 1900 to surfaces, such as a vessel or the myocardium of a heart.

Optionally, the active fixation device 1900 includes regions having decreased wall thickness and/or creases around a radius of the device 1900. The push tube 122 operates to compress these regions and form at least one radial projection extending around the active fixation device. In another option, the openings 1906A-C extend helically around the active fixation device 1900. Pushing or twisting of the push tube 122 operates to correspondingly compress or twist the active fixation device 1900 and extend the members 1912A-C. In still another option, the active fixation device 1900 includes only openings 1906A to form radially projecting members 1912A and/or tines 1914A. The active fixation device 1900, in yet another option, includes a single opening 1906A and a single member 1912A is adjacent to the opening 1906A.

Optionally, the active fixation device 1900 includes cavities that form a mesh pattern in the device 1900 so the device 1900 has a weakened column strength between the proximal end 1904 and the flange 1902. When compressed or twisted, the mesh pattern bows away from the elongate body 102 to form at least one projection. The active fixation device 1900 includes elongate elements (e.g. wires, ribbons or the like), in one option. The elements bow away from the elongate body 102, when compressed or twisted by the push tube 122, to form at least one radially projecting member. The elements, optionally, include, but are not limited to, super-elastic metals, such as Nitinol. In another option, the elements are formed with a microcoil including a film (e.g. 0.001 inches thick) that is wrapped into a coil. Optionally, the elements are woven or braided into a mesh and the mesh bows away from the elongate body 102, when compressed or twisted.

In another option, the active fixation device 1900 is radiopaque to facilitate visualization of the device 1900 during implantation procedures. Optionally, the active fixation device 1900 includes a conductive material (e.g. Nitinol) and acts as an electrode when coupled with the conductor 110 (FIG. 1). One or more of the active fixation device 1900, the elongate body 102 and the push tube 122 include fluoropolymers, in yet another option, to facilitate sliding movement between the push tube 122 and the elongate body 102 and/or the device 1900 and the elongate body 102. Optionally, a lubricious coating is applied between one or more of the active fixation device 1900, the elongate body 102 and the push tube 122 to facilitate sliding movement therebetween. In a further option, one or more of the active fixation device 1900 and the push tube 122 are coextruded with a lubricous polymer forming the inner diameter.

In operation, the lead assembly 100 including the active fixation device 1900 having openings 1906A is positioned within the vasculature, for instance, the tortuous vasculature around the left side of the heart. As shown in FIG. 19E, in one option, the active fixation device 1900 is in a first unexpanded position during navigation of the lead assembly 100 through the vasculature. When the lead assembly 100, including optionally the electrode 112, is positioned where desired, the push tube 122 is advanced toward the active fixation device 1900. Referring now to FIG. 19F, the push tube 122 transmits pushing forces to the proximal end 1904 thereby compressing the active fixation device 1900. Compression of the active fixation device 1900 radially expands the members 1912A from the device 1900. The active fixation device 1900 assumes a second radially expanded position. The members 1912A engage against a surrounding surface (e.g. a vessel wall and/or the myocardium of a heart). In another option, the push tube 122 is further advanced toward the active fixation device 1900 and the members 1912A fold back on themselves to form tines 1914A (FIG. 19D).

Referring again to FIG. 19F, a gap 1916 is formed between the push tube 122 and the lead terminal 1918. To retain the active fixation device 1900 at the desired location on the elongate body 102 and/or in the compressed state a stop 1920, such as a suture sleeve, is disposed within the gap 1916. The stop 1920, in one option, is sized and shaped to snugly fit within the gap 1916 and overlay a portion of the push tube 122 and the lead terminal 1918 (e.g. a flexible boot proximal to electrical terminal contacts). Optionally, a spacer clip is placed within the gap 1916 to immobilize the active fixation device 1900, and the stop 1920 covers the spacer clip. In another option, the stop 1920 is deformable and slid over the lead terminal 1918 to position the stop 1920 within the gap 1916. In yet another option, the stop 1920 is formed around the push tube 122 distal to the lead terminal 1918 and slid into the gap 1916 after expansion of the active fixation device 1900. Optionally, the stop 1920 is slit along one side and pressed over the elongate body 102 and the push tube 122 to retain the active fixation device 1900 at the desired location and/or in the compressed state with the members 1912A extended. In another option, suturing is performed around the stop 1920 to snugly engage the stop 1920 to the elongate body 102 and immobilize the active fixation device 1900.

Optionally, removal of the stop 1920 from within the gap 1916 permits removal of the lead assembly 100 from within the vasculature. In one option, the stop 1920 is deformed to pull the stop 1920 out of the gap 1916. The push tube 122 is pulled toward the lead terminal 1918, optionally, and away from the active fixation device 1900. The active fixation device 1900 includes, in another option, a deformable material (e.g. polyurethane) and longitudinally expands to assume the profile shown in FIG. 19E as the push tube 122 is retracted. In one option, the active fixation device 1900 radially contracts as the device 1900 longitudinally expands. Optionally, the push tube 122 is coupled to the proximal end 1904 of the active fixation device 1900 and pulling of the push tube 122 correspondingly pulls and longitudinally expands the device 1900 as shown in FIG. 19E. The lead assembly 100 with the radially contracted active fixation device 1900 is retracted out of the vasculature.

Figure 20:
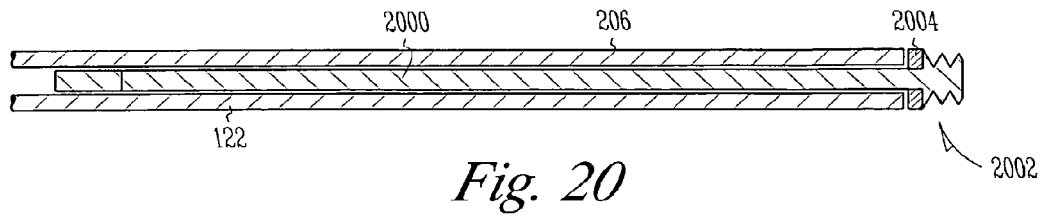
FIG. 20 is a cross-sectional view of an active fixation device and a push tube constructed in accordance with another embodiment.

FIG. 20 is a cross sectional view of an active fixation device 2000 substantially surrounded by the push tube 122. In one option, the active fixation device 2000 is a deformable cable. In another option, the active fixation device 2000 has a predetermined non-linear shape, for instance, a spiral, zigzag or the like. The deformable cable, in one option, includes a shape memory material such as Nitinol. In another option, in larger vessels and/or with less tortuous vasculature, the deformable cable is formed with filars coiled in a pattern to provide the predetermined non-linear shape. The active fixation device 2000 is preformed with the predetermined shaped (e.g., a molded polymer or the like), in yet another option.

The push tube 122 is formed of a sufficiently rigid material (e.g. stainless steel, polymer or polymer including a metal braid) to straighten the active fixation device 2000 when the push tube 122 is coupled around the device 2000. In one option, the push tube 122 is slidably coupled to the active fixation device 2000 and moved over the device 2000 toward a distal end 2002 of the device 2000. The push tube 122 straightens the non-linear shape of the active fixation device 2000 as it is moved over the device 2000. In another option, where the active fixation device 2000 includes Nitinol, the predetermined shape is straightened prior to coupling with the push tube 122 and heat (e.g., body heat) is used to provide the predetermined non-linear shape. Optionally, the push tube 122 provides column strength to the active fixation device 2000 to move the device 2000 toward the distal end of the elongate body 2100 (See FIG. 21).

In one option, a seat 2004 sized and shaped to receive the push tube distal end 206 is coupled to the active fixation device 2000. The seat 2004, in another option, extends radially from the distal end 2002 of the active fixation device 2000. In yet another option, the seat is crimped, welded or the like around the active fixation device 2000. The seat 2004 and the push tube distal end 206 include, optionally, a key and corresponding notch to prevent relative rotation between the push tube 122 and the active fixation device 2000. In another option, the push tube distal end 206 and the seat 2004 are non-circular and engage against each other to prevent relative rotation therebetween. The push tube 122, in yet another option, is rotated to turn the active fixation device 2000 and couple the device 2000 with the elongate body 2100, described below.

Figure 21:
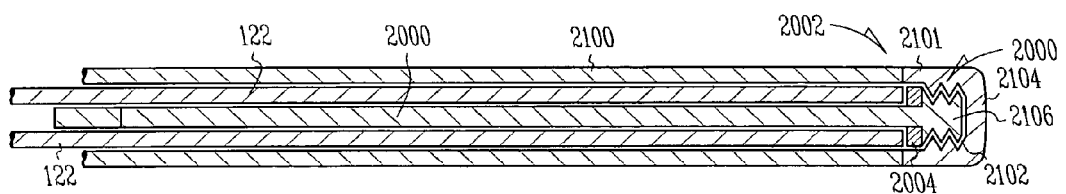
FIG. 21 is a detailed cross-sectional view of a portion of a lead and an active fixation device and a push tube constructed in accordance with another embodiment.

FIG. 21 is a cross sectional view of the elongate body 2100 slidably coupled around the active fixation device 2000 and the push tube 122. Optionally, the elongate body 2100 includes a distal tip 2101. The distal tip 2101 is deformable (e.g. silicone rubber), in another option, to facilitate navigation in tortuous vasculature, such as around the left side of a heart. Where the active fixation device 2000 is a deformable cable, the deformable cable has a sufficiently small profile to permit navigation of the correspondingly sized elongate body 2100 through tortuous vasculature. In one option, the elongate body 2100 includes a fastener 2102 substantially adjacent to a distal end 2104. In another option, the fastener 2102 includes threading that extends around the distal end 2004 of the active fixation device 2000. In yet another option, the fastener 2102 includes a snap fitting, adhesive or the like. The fastener 2102 is sized and shaped to securely couple the distal end 2002 of the active fixation device 2000 to the distal end 2104 of the elongate body 2100. In another option, the distal end 2004 of the active fixation 2000 device includes a corresponding fastener 2106 sized and shaped to engage with the fastener 2102 and securely couple the device 2000 to the elongate body 2100. Optionally, the active fixation device 2000 is immobilized with respect to the elongate body 2100 when coupled to the elongate body 2100. The active fixation device fastener 2106, in an option, includes threading corresponding to the threading of the fastener 2102. The push tube 122 engages against the seat 2004 and moves the active fixation device through the elongate body 2100 toward the distal end 2104, in one option. In another option, the push tube 122 is rotated to couple the fastener 2102 with the active fixation device 2000 (e.g. the active fixation device fastener 2106) substantially adjacent to the distal end. Optionally, the threading of the fastener 2106 engages with corresponding threading on the fastener 2102.

Figure 22:
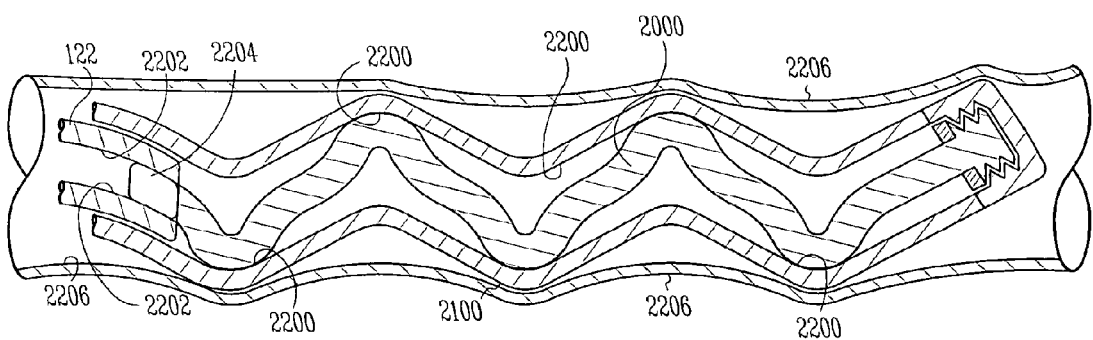
FIG. 22 is a detailed cross-sectional view of a portion of a lead and an active fixation device and a push tube constructed in accordance with another embodiment.

FIG. 22 is a cross sectional view of the active fixation device 2000 engaged against an inner surface 2200 of the elongate body 2100. In one option, the push tube 122 is withdrawn from around the active fixation device 2000 to allow the device 2000 to assume the predetermined non-linear shape. In another option, the push tube 122 is withdrawn and the active fixation device 2000 including Nitinol is exposed to heat (e.g., body heat). The heat induces the active fixation device 2000 to assume the non-linear predetermined shape and engage against the elongate body 2100. Engagement of the active fixation device 2000 with the inner surface 2200 moves the elongate body 2100 into a non-linear shape corresponding to the predetermined nonlinear shape of the active fixation device. In one example, the elongate body 2100 assumes a corresponding non-linear shape when the non-linear active fixation device 2000 engages against the inner surface 2200. The elongate body 2100 correspondingly engages against a surface 2206 such as the wall of a vein or artery and/or the myocardium of a heart, in one option, and immobilizes the elongate body 2100 within the vasculature.

Figure 23:
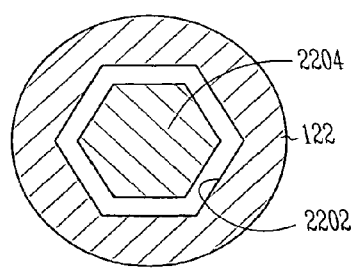
FIG. 23 is a sectional view of a push tube and an active fixation device constructed in accordance with another embodiment.

In another option, at least a portion of the inner perimeter 2202 of the push tube 122 is non-circular. The active fixation device optionally includes a lug 2204 having a corresponding size and shape to the non-circular inner perimeter 2202 of the push tube 122. As the push tube 122 is withdrawn from around the active fixation device 2000, as shown in FIG. 22, the inner perimeter 2202 of the push tube 122 is coupled around the lug 2204. One example of the coupling between the push tube 122 and the lug 2204 is shown in the sectional view of FIG. 23. The inner surface 2202 has a hexagonal geometry, in the example shown. In another example, the inner surface 2202 has a triangular, square, ovular geometry or the like. The outer perimeter of the lug 2204 has a corresponding non-circular geometry. In another option, the active fixation device is coupled around the push tube and the active fixation device has a non-circular inner perimeter and the push tube has a corresponding non-circular outer perimeter.

Optionally, the push tube 122 is rotated and the non-circular inner perimeter 2202 engages against the corresponding non-circular lug 2204 to rotate the active fixation device 2000 as desired. Referring again to FIG. 22, in one option, the active fixation device 2000 is rotated within the elongate body 2100 to twist the device 2000 and correspondingly twist the elongate body 2100 coupled thereto. In one example, the active fixation device 2000 is rotated to improve contact between the elongate body (e.g. electrodes coupled to the elongate body) and the surface 2206, for instance, the electrically active myocardium of the heart. In another example, the active fixation device 2000 is rotated to change the engagement of the elongate body 2100 with the surface 2206, for instance, to enhance the immobilization of the elongate body 2100 within the vasculature.

FIG. 24 is a block diagram illustrating a method 2400 for positioning a lead assembly (e.g., a side rail lead assembly). At 2402, the lead assembly is guided over a guide wire. The guide wire is slidably coupled to a side rail seat. The side rail seat is substantially adjacent to the distal end of the lead assembly and disposed along the lead (e.g. juxtaposed to the lead). At 2404, a push tube is moved over the guide wire and the side rail seat and the lead correspondingly move with the push tube. In one option, the push tube is slidably coupled around the guide wire. The push tube is coupled to the side rail seat in another option. In another option, the method 2400 includes coupling the push tube with the side rail seat. Coupling the push tube with the side rail seat includes, optionally, seating at least a push tube distal end within a socket in the side rail seat. In one option, a surface defining the socket is sized and shaped to immobilize at least the push tube distal end. In yet another option, the side rail seat and the lead assembly are rotated with the push tube. The push tube is twisted to rotate the side rail seat and the lead assembly, in one option. Optionally, coupling the push tube with the side rail seat includes coupling a push tube distal end having a key with the side rail seat having a corresponding recess. The method 2400, in another option, includes deflecting at least a push tube distal end, wherein the push tube distal end is more flexible than another portion of the of push tube. Optionally, the guide wire is exchanged for a second guide wire. In one option, relative to the guide wire, the second guide wire has a different flexibility or predetermined shape.

In one option, the method 2400 includes moving an active fixation device over the guide wire toward the lead assembly distal end with the push tube, wherein the push tube is coupled to the active fixation device. In another option, the push tube is uncoupled from the side rail seat to couple with the active fixation device. The active fixation device is coupled with a distal tip, optionally, and the distal tip is coupled to the elongate body substantially adjacent to the distal end. In one option, a combined outer perimeter of the active fixation device and the distal tip is greater than an outer perimeter of the distal tip. In another option, the active fixation device is coupled with the distal tip by engaging a pawl with a rack and inhibiting movement of the active fixation device away from the distal tip. In yet another option, the active fixation device is immobilized in surrounding tissue. The active fixation device, in one example, is immobilized by wedging the active fixation device and the distal tip within a vein or artery. In another example, the active fixation device expands to immobilize the device in the surrounding tissue. Optionally, immobilizing the active fixation device includes disposing a tine in the surrounding tissue.

The above described lead assembly allows for implantation of slender leads through tortuous vasculature (e.g. coronary veins around the left side of the heart) using a push tube. In one option, the lead assembly includes a distal tip sized and shaped to couple with a push tube that extends along at least a portion of the elongate body. A pushing force is applied to the push tube and transmitted to the distal tip to push the distal end of the elongate body through vasculature and into or around the heart (e.g., into the epicardium of the heart). In one option, a portion of the elongate body proximal to the distal tip and coupled thereto is pulled as the distal tip is pushed by the push tube. In another option, the distal tip includes a seat. The push tube and the seat include, optionally, non-circular perimeters or a key and a recess. The push tube is rotated to correspondingly rotate the distal tip into a desired orientation for optimum electrode to tissue contact, in one option. In another option, the push tube is rotated to turn the distal tip and the elongate body and allow for easier navigation of the vasculature.

Because the push tube is fed over the guide wire or over the elongate body, a stylet lumen or the like is not necessary. In one option, the elongate body has a has a smaller cross-section and is less invasive than leads having a stylet lumen. The lead assembly includes additional conductors or the like in the space occupied by a stylet lumen, in another option. The conductors of the lead assembly described herein include cables that extend substantially linearly along the elongate body because a stylet lumen formed with coiled conductors is not necessary. Linear cables take up less space within the elongate body, as compared to coiled conductors, and allow for a lead assembly with a smaller outer perimeter that also has multiple conductors and corresponding electrodes. In yet another option, a lumen is formed within the elongate body and is sized and shaped to receive the push tube and the guide wire and the push tube is fed over the guide wire to navigate the elongate body through vasculature. Having a push tube lumen within the elongate body decreases the profile of the elongate body allowing for easier navigation of the lead assembly. Additionally, the push tube provides increased column strength compared to, for example, a stylet. The increased column strength enhances the transmission of pushing forces through the push tube to the elongate body.

Moreover, the push tube (e.g. tubing, integral tubing, catheter, or the like) of the lead assembly allows for the positioning of a variety of active fixation devices into desired orientations along the elongate body, for instance, after the elongate body is positioned within vasculature and/or a heart. The elongate body tracks through the vasculature easily without the active fixation devices disposed along the elongate body until after implantation of the elongate body. In one option, the active fixation devices have a larger profile than the elongate body and are introduced after the elongate body is positioned as desired within a heart and/or the vasculature. In another option, when the active fixation device and distal tip are coupled the combined outer perimeter engages the surrounding vasculature of, for example, a vein or artery, and securely couples the elongate body with the vasculature. In another option, active fixation devices sized and shaped to deform the elongate body are advanced along the elongate body. In one option, the active fixation devices deform and push the elongate body (e.g. including electrodes) into snug engagement with the vasculature. In another option, active fixation devices are actuated with the push tube (e.g. by rotating the push tube to turn a threaded fixation device) to couple with surfaces within the vasculature or on the epicardial surfaces of a heart.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the invention should, therefore, be determined with reference to the appended claims, along with the full scope of equivalents to which such claims are entitled.

What is claimed is:

1. An apparatus comprising:
   an elongate body extending from a proximal end to a distal end;
   a conductor disposed within the elongate body;
   an electrode coupled to the elongate body, wherein the electrode is in electrical communication with the conductor;
   a push tube extending along at least a portion of the elongate body; and
   a distal tip coupled to the elongate body substantially adjacent to the distal end, wherein the distal tip is sized and shaped to couple with a push tube distal end and at least a portion of an outer perimeter of the distal tip includes a seat sized and shaped to receive a push tube distal end, wherein the seat includes a socket sized and shaped to grasp and immobilize the push tube distal end, and wherein the seat includes a deformable coil disposed within the socket, and the deformable coil has an inner perimeter smaller than the outer perimeter of the push tube.

2. The apparatus of claim 1, wherein at least one of the push tube distal end and the seat has a noncircular outer perimeter and the other of the push tube distal end and the seat has a corresponding inner perimeter.

3. The apparatus of claim 1, wherein the elongate body is substantially adjacent to the push tube and the seat.

4. The apparatus of claim 1, wherein the outer perimeter of the distal tip tapers from a proximal portion of the distal tip toward a distal portion of the distal tip.

5. The apparatus of claim 1, wherein the distal tip includes an active fixation device.

6. The apparatus of claim 5, wherein the active fixation device includes at least one slot extending substantially along the active fixation device.

7. The apparatus of claim 1, wherein the distal tip includes an exit groove sized and shaped to immobilize at least a portion of the elongate body.

8. The apparatus of claim 1, wherein at least a first portion of the push tube is more flexible than a second portion of the push tube.

9. The apparatus of claim 8, wherein the push tube distal end is more flexible than the second portion of the push tube.

10. The apparatus of claim 8, wherein at least the portion of the push tube includes a groove extending at least part way between an outer perimeter of the push tube and an inner perimeter of the push tube.

* * * * *